(12) United States Patent
Dusbabek et al.

(10) Patent No.: US 6,203,558 B1
(45) Date of Patent: Mar. 20, 2001

(54) STENT DELIVERY SYSTEM HAVING STENT SECUREMENT APPARATUS

(75) Inventors: Andrew J. Dusbabek, Dayton; Louis G. Ellis, St. Anthony; Christopher R. Larson, St. Paul; Terry V. Brown, Fridley; Charles L. Euteneuer, St. Michael; Steven P. Mertens, Plymouth; Richard C. Mattison, Zimmerman; David J. Blaeser, Champlin; Linda R. Lorentzen Cornelius, Wayzata; Martin R. Willard, Maple Grove; Fernando Di Caprio, Mendota Heights; Stanley A. Nordin, Monticello, all of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/418,277

(22) Filed: Oct. 14, 1999

Related U.S. Application Data

(63) Continuation of application No. 08/916,554, filed on Aug. 22, 1997, now Pat. No. 5,968,069, which is a continuation-in-part of application No. 08/807,791, filed on Feb. 28, 1997, now Pat. No. 6,077,273, application No. 08/702,150, filed on Aug. 23, 1996, now Pat. No. 6,007,543, application No. 08/697,453, filed on Aug. 23, 1996, now abandoned, and application No. 08/701,979, filed on Aug. 23, 1996.

(51) Int. Cl.[7] ................................ A61B 29/00; A61M 29/00; A61F 11/00

(52) U.S. Cl. ........................... 606/198; 606/194; 606/108

(58) Field of Search .................................. 606/194, 198, 606/200, 108, 195; 604/96

(56) References Cited

U.S. PATENT DOCUMENTS

| | | |
|---|---|---|
| 2,690,595 | 10/1954 | Raiche . |
| 4,271,839 | 6/1981 | Fogarty et al. . |
| 4,327,736 | 5/1982 | Inoue . |
| 4,403,612 | 9/1983 | Fogarty . |
| 4,576,871 | 3/1986 | Oestreich . |
| 4,637,396 | 1/1987 | Cook . |
| 4,649,914 | 3/1987 | Kowalewski . |
| 4,702,252 | 10/1987 | Brooks et al. . |
| 4,763,654 | 8/1988 | Jang . |
| 4,787,388 | 11/1988 | Hofmann . |
| 4,885,194 | 12/1989 | Tight, Jr. et al. . |
| 4,932,958 | 6/1990 | Reddy et al. . |
| 4,983,167 | 1/1991 | Sahota . |
| 4,990,139 | 2/1991 | Jang . |
| 4,994,033 | 2/1991 | Shokey et al. . |
| 5,049,131 | 9/1991 | Deuss . |
| 5,057,092 | 10/1991 | Webster, Jr. . |
| 5,071,406 | 12/1991 | Jang . |
| 5,090,958 | 2/1992 | Sahota . |

(List continued on next page.)

Primary Examiner—Michael Buiz
Assistant Examiner—(Vikki) Hoa B. Trinh
(74) Attorney, Agent, or Firm—Vidas, Arrett & Steinkraus

(57) ABSTRACT

A system/assembly for delivery and deployment of an inflation expandable stent within a vessel, comprising a catheter having proximal and distal ends; a stent, inflation expandable from a delivery diameter to a deployment diameter, such that the delivery diameter is reduced from the deployment diameter for conforming the stent to the catheter, such that the stent, in its delivery diameter, is coaxially mounted on the catheter near the catheter distal end; an expandable inflation member coaxially mounted on the catheter axially within the stent, for expansion of the stent from the delivery diameter to the deployment diameter upon application of fluid deployment pressure to the inflation member; and a securement component coaxially mounted on the catheter, axially within the expandable inflation members, the securement component designed and adapted to provide a securement pressure to the stent in the delivery diameter to maintain the stent in position on the catheter during delivery to the deployment site.

22 Claims, 21 Drawing Sheets

U.S. PATENT DOCUMENTS

| | | |
|---|---|---|
| 5,096,848 | 3/1992 | Kawamura . |
| 5,108,370 | 4/1992 | Walinsky . |
| 5,195,969 | 3/1993 | Wang et al. . |
| 5,264,260 | 11/1993 | Saab . |
| 5,270,086 | 12/1993 | Hamlin . |
| 5,295,962 | 3/1994 | Crocker et al. . |
| 5,298,300 | 3/1994 | Hosoi et al. . |
| 5,304,132 | 4/1994 | Jang . |
| 5,306,250 | 4/1994 | March et al. . |
| 5,344,401 | 9/1994 | Radisch et al. . |
| 5,344,402 | 9/1994 | Crocker . |
| 5,348,538 | 9/1994 | Wang et al. . |
| 5,358,487 | 10/1994 | Miller . |
| 5,378,237 | 1/1995 | Boussignac et al. . |
| 5,415,635 | 5/1995 | Bagaoisan et al. . |
| 5,478,320 | 12/1995 | Trotta . |
| 5,490,839 | 2/1996 | Wang et al. . |
| 5,571,089 * | 11/1996 | Crocker ................. 604/102 |
| 5,587,125 | 12/1996 | Roychowdhury . |
| 5,643,278 * | 7/1997 | Wijay .................. 606/108 |
| 5,653,691 * | 8/1997 | Rupp et al. ............ 604/96 |
| 5,882,335 * | 3/1999 | Leone et al. ........... 604/96 |

* cited by examiner

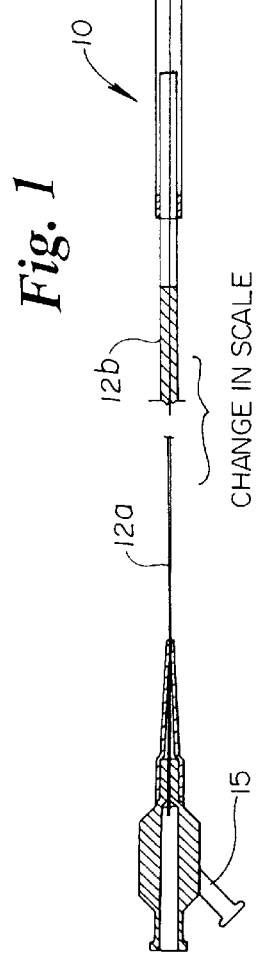
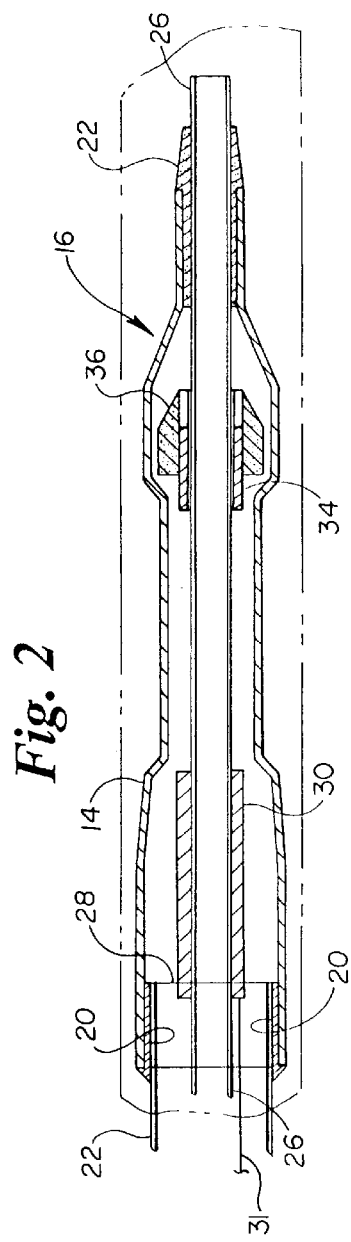

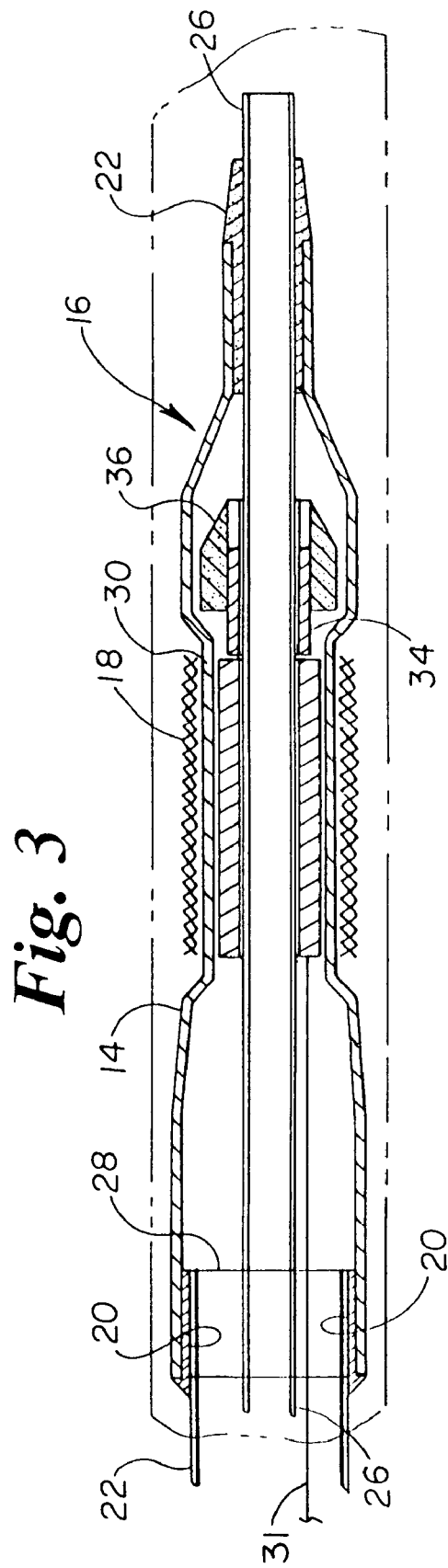

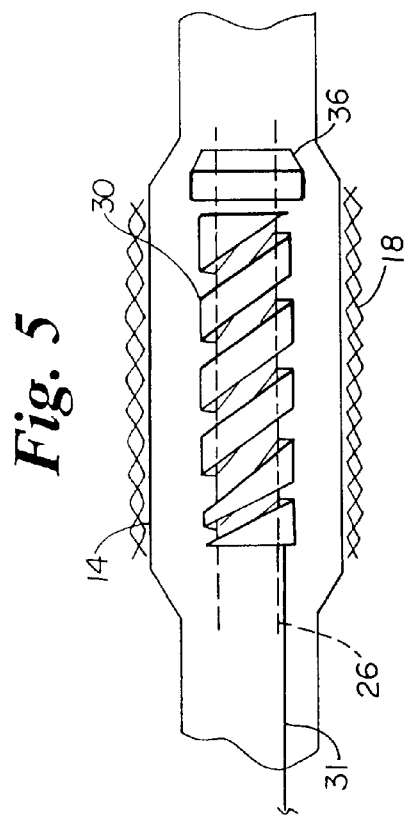
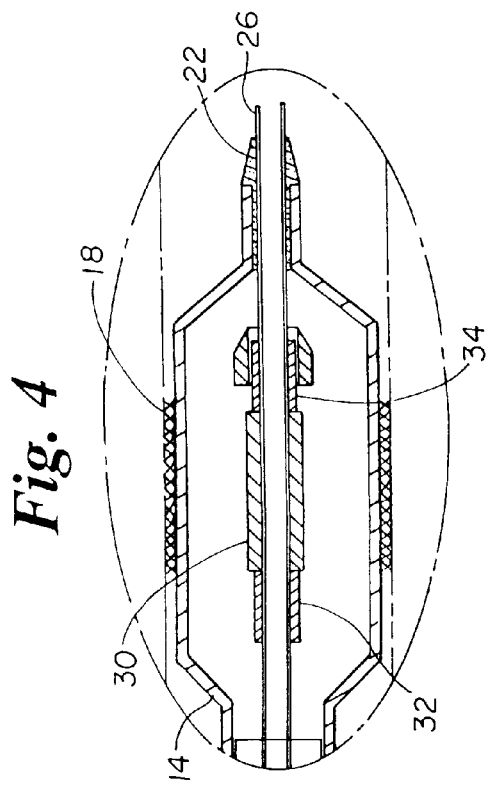
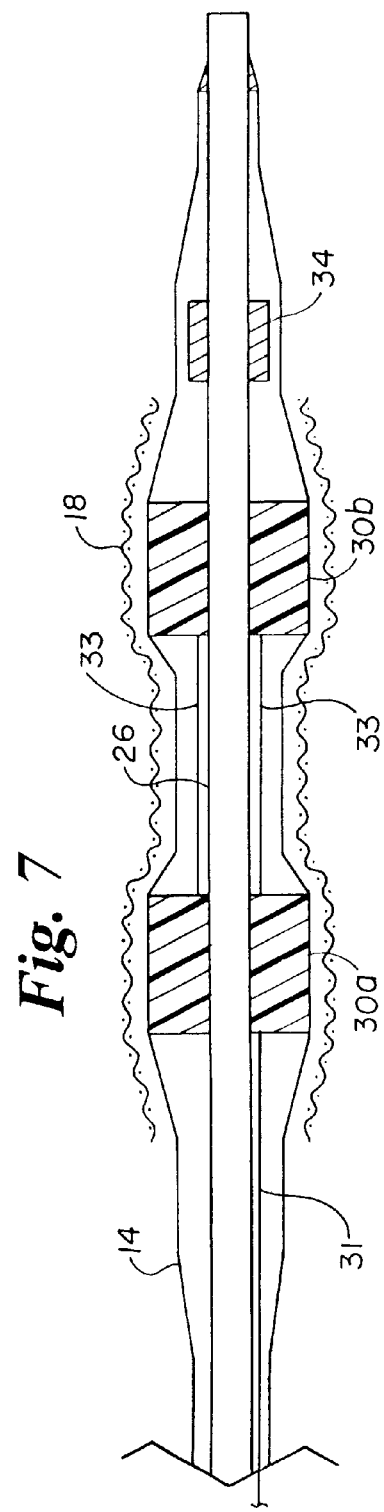

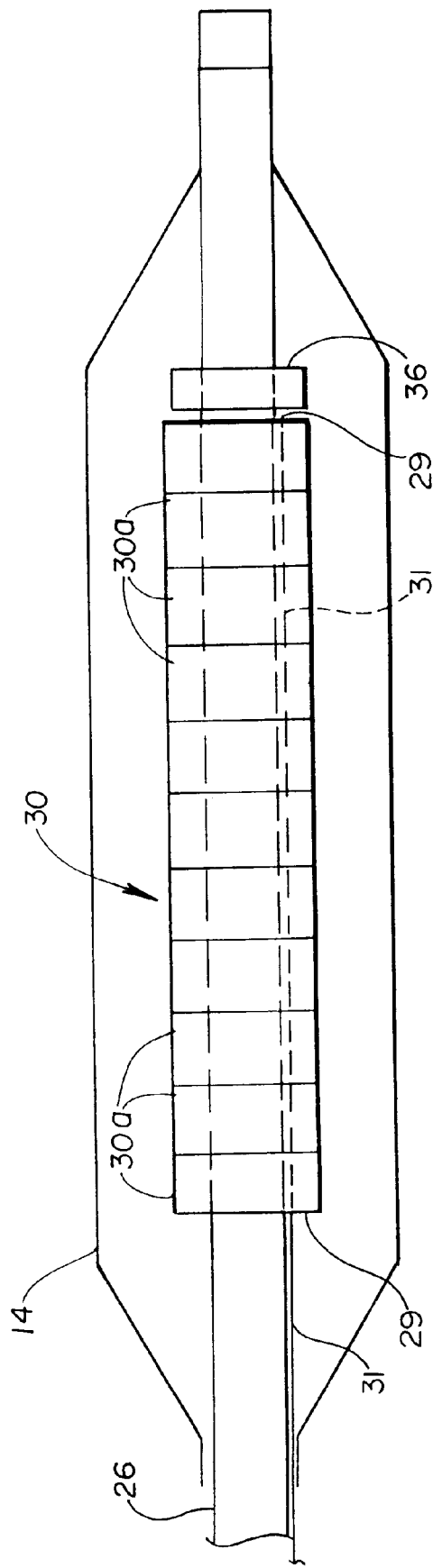

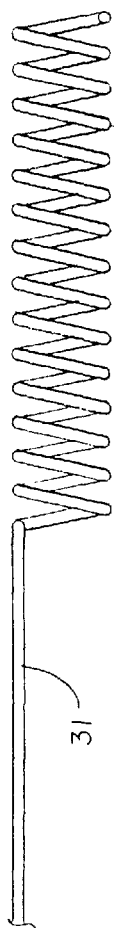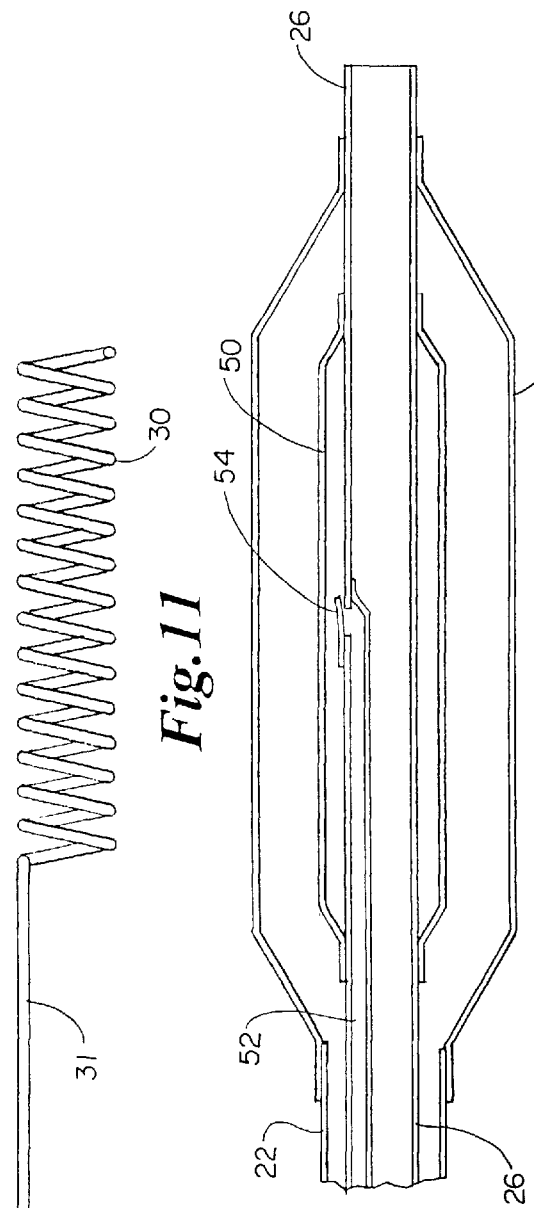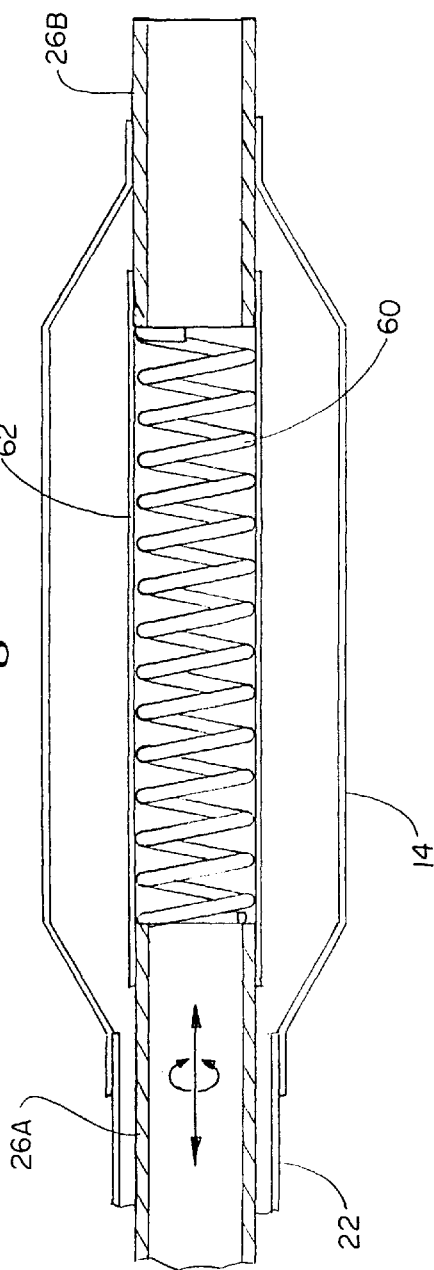

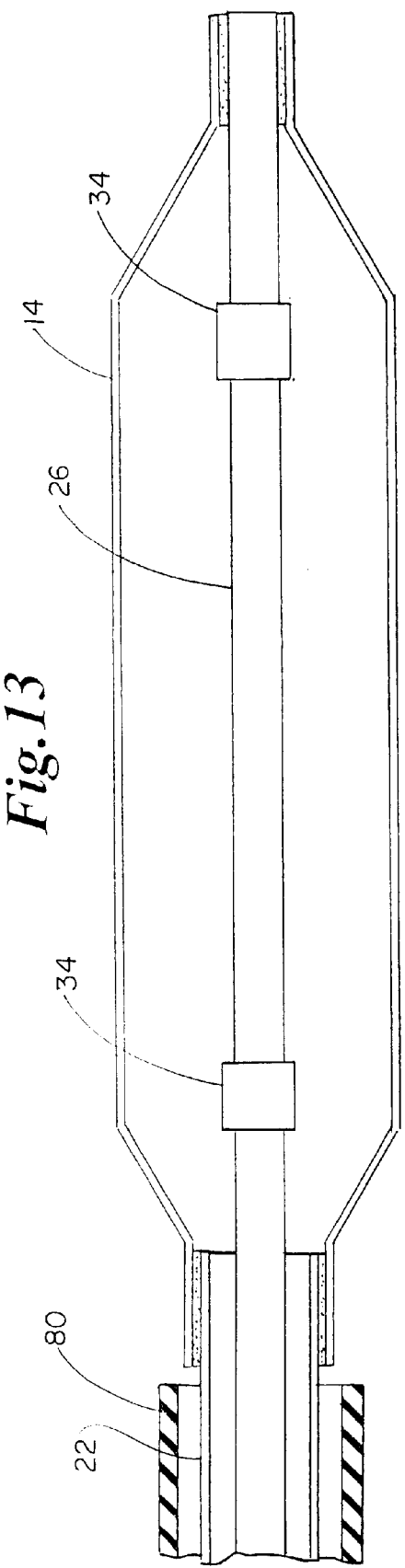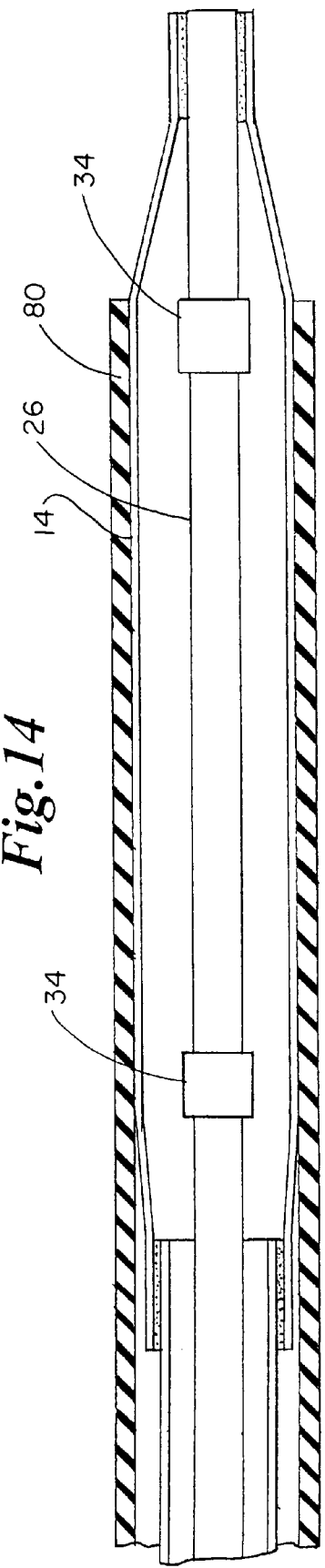

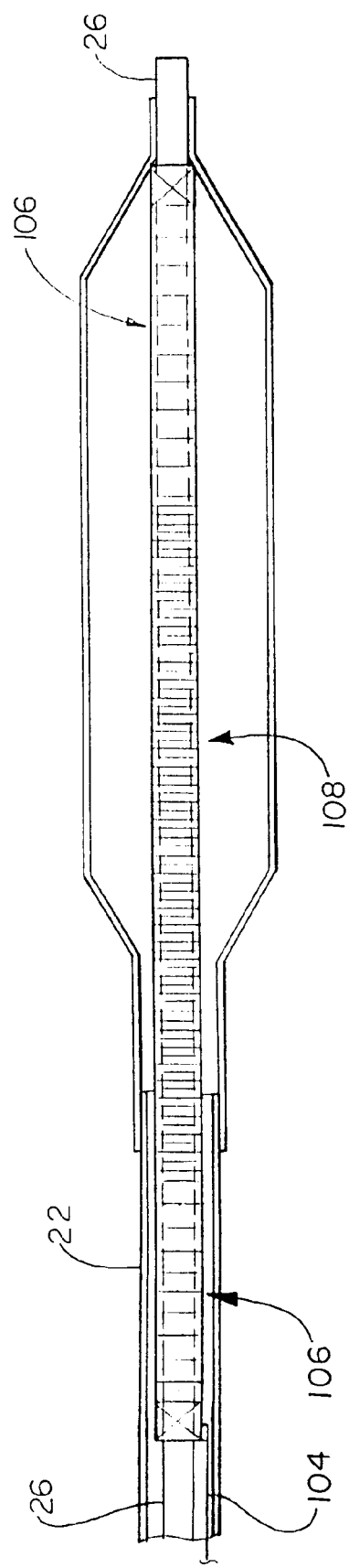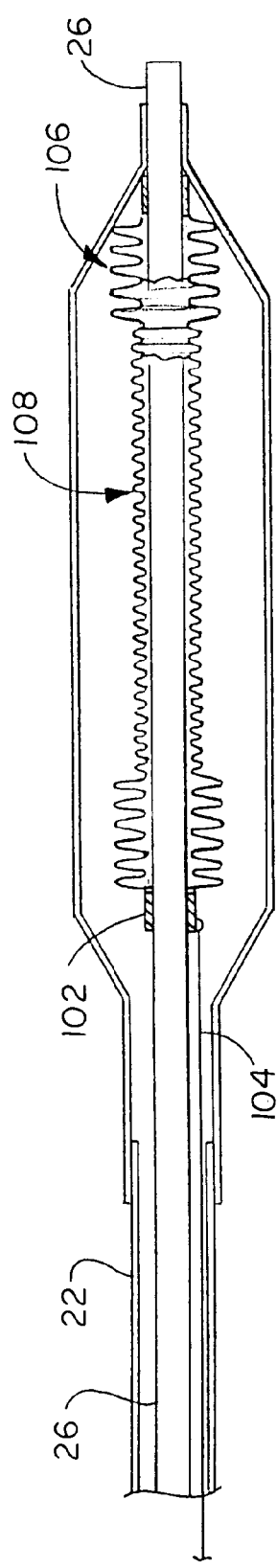
Fig.15
Fig.16

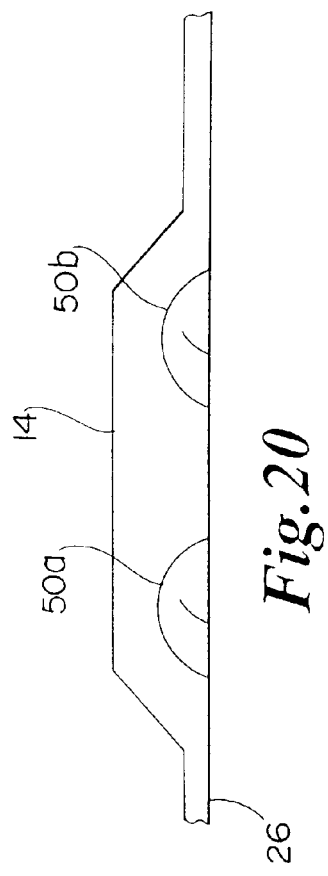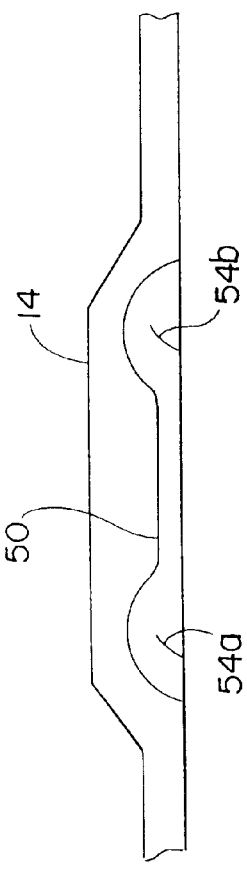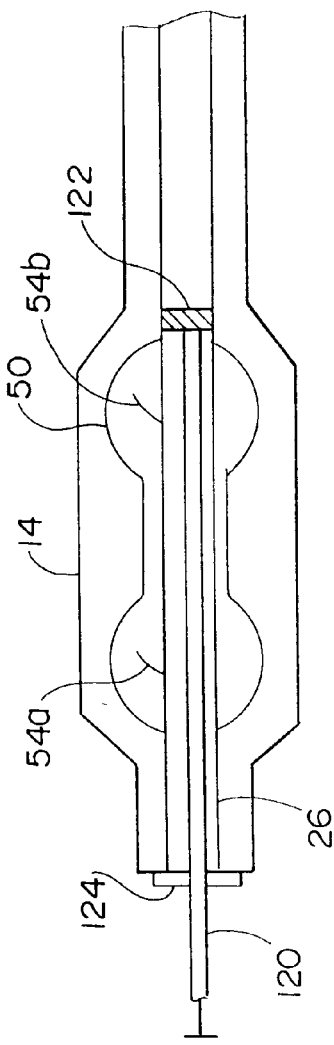

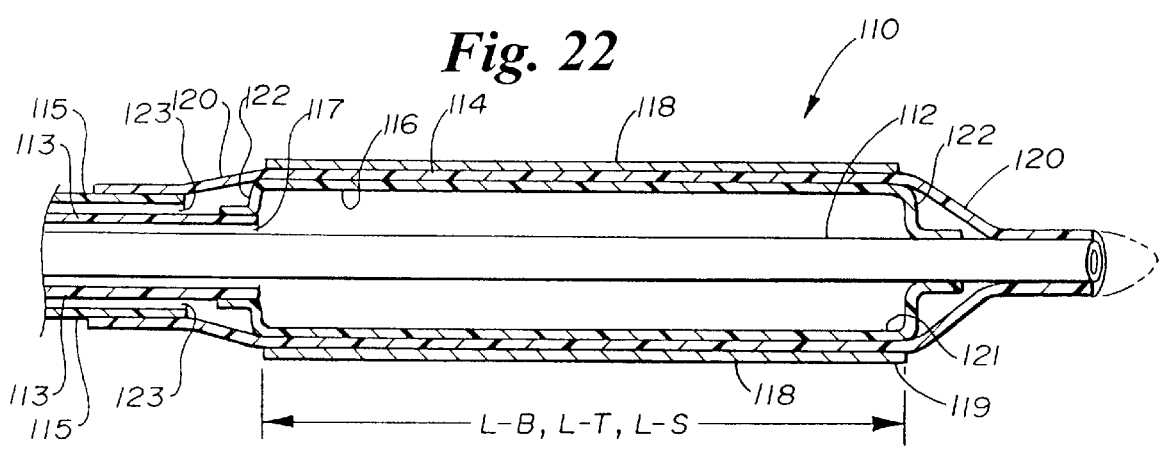
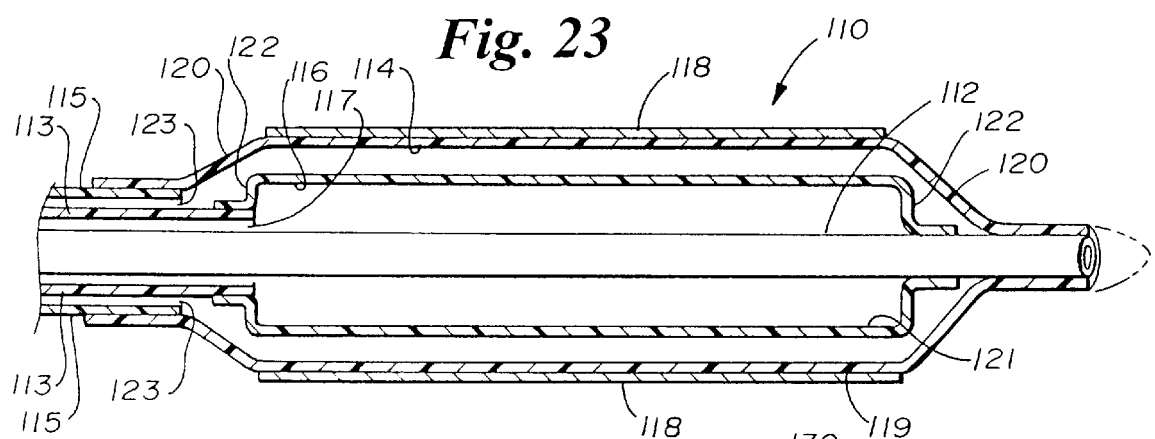
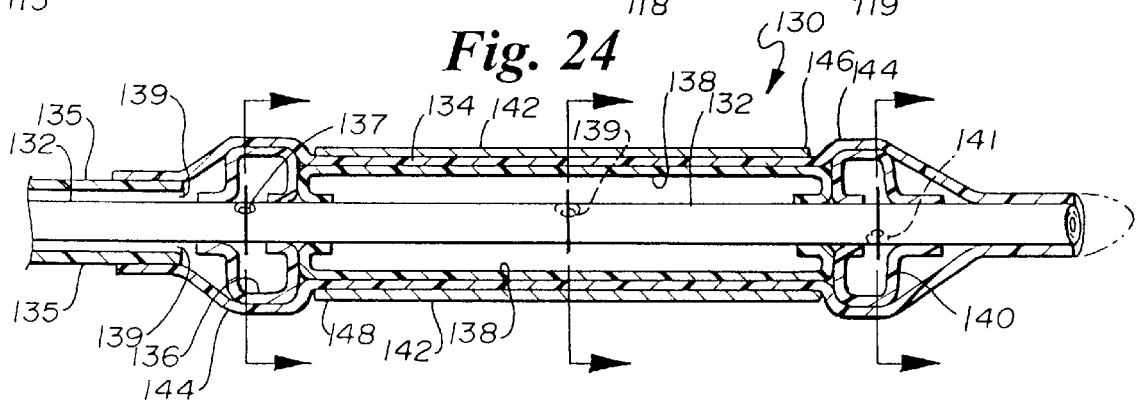
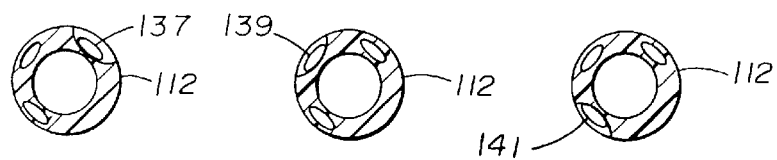

STENT DELIVERY SYSTEM HAVING STENT SECUREMENT APPARATUS

The present application is a continuation of U.S. application Ser. No. 08/916,554, filed Aug. 22, 1997, now U.S. Pat. No. 5,968,069, which is a Continuation-in-part application based on U.S. Ser. No. 08/807,791 Feb. 28, 1997, now U.S. Pat. No. 6,077,273, U.S. Ser. No. 08/702,150 filed Aug. 23, 1996, now U.S. Pat. No. 6,007,543, U.S. Ser. No. 08/697,453 filed Aug. 23, 1996, and U.S. Ser. No. 08/701,979, filed Aug. 23, 1996, all of which are incorporated by reference in their entirety.

FIELD OF THE INVENTION

This invention relates to an assembly and method for delivering and deploying an inflation expandable stent, particularly within a lumen of a body vessel. More specifically, this invention relates to stent securement devices most notably positioned between the balloon and the inner shaft of the catheter.

BACKGROUND OF THE INVENTION

Stents and stent delivery assemblies are utilized in a number of medical procedures and situations, and as such their structure and function are well-known. A stent is a general cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well-known and widely available. Self-expanding stents must be maintained under positive external pressure in order to maintain their reduced diameter configuration during delivery of the stent to its deployment site. Inflation expandable stents (also known as balloon expandable stents) are crimped to their reduced diameter about the delivery catheter, positioned at the deployment site, and then expanded to the vessel by diameter by fluid inflation of the balloon positioned between the stent and the delivery catheter. The present invention is particularly concerned with enhanced stent securement and safer stent loading in the delivery and deployment of balloon expandable stents.

In angioplasty procedure, there may be restenosis of the artery, which either necessitates another angioplasty procedure, a surgical bi-pass procedure, or some method of repairing or strengthening the area. To prevent restenosis and strengthen the area, a physician can implant an intravascular prosthesis for maintaining vascular patency, i.e. a stent, inside the artery at the lesion. The stent is expanded to a larger diameter for placement in the vasculature, often by the balloon portion of the catheter. Stents delivered to a restricted coronary artery, expanded to a larger diameter as by a balloon catheter, and left in place in the artery at the site of a dilated lesion are shown in U.S. Pat. No. 4,740,207 to Kreamer; U.S. Pat. No. 5,007,926 to Derbyshire; U.S. Pat. No. 4,733,665 to Palmaz; U.S. Pat. No. 5,026,377 to Burton et al.; U.S. Pat. No. 5,158,548 to Lau et al.; U.S. Pat. No. 5,242,399 to Lau et al.; U.S. Pat. No. 5,344,426 to Lau et al.; U.S. Pat. No. 5,415,664 to Pinchuck; U.S. Pat. No. 5,453,090 to Martinez et al.; U.S. Pat. No. 4,950,227 to Savin; U.S. Pat. No. 5,403,341 to Solar; U.S. Pat. No. 5,108,416 to Ryan et al.; and European Patent Application No. 707837A1 to Scheiban, all of which are incorporated herein by reference. A stent particularly preferred for use with this invention is described in PCT Application No. 96/03092-A1, published Feb. 8, 1996, the content of which is incorporated herein by reference.

In advancing a balloon expandable stent through a body vessel to the deployment site, there are a number of important considerations. The stent must be able to securely maintain its axial position on the delivery catheter. The stent, particularly its distal and proximal ends, are sometimes protected to prevent distortion of the stent, and minimize trauma to the vessel walls. Balloon expandablestent delivery and deployment assemblies are known which utilize restraining means that overlay the stent during delivery. U.S. Pat. No. 4,950,227 to Savin et al., relates to a balloon expandable stent delivery system in which a sleeve overlaps the distal or proximal margin (or both) of the stent during delivery. During inflation of the stent at the deployment site, the stent margins are freed of the protective sleeve(s) and the sleeves then collapse toward the delivery catheter for removal. A number of balloon expandable stent delivery and deployment assemblies do not use overlaying restraining members, such as the Savin sleeves, to position the stent for delivery. European Patent Application No. EP 055 3960A1 to Lau et al., uses an elastic sheath interspaced between the balloon and the stent. The sheath is said to act as a barrier to protect the balloon from the stent, allow uniform stent expansion, decrease balloon deflation time, prevent undesirable balloon flattening upon deflation and provide a friction substrate for the stent. The Lau sheath can be positioned on the inside or outside of the balloon. U.S. Pat. No. 5,409,495 to Osborne, similarly uses an elastic sleeve or sheath surrounding and in contact with the balloon for controlling the balloon radial expansion. In addition, Osborne is said to use restraining bands or a pair of balloons to achieve controllable stent expansion characteristics. U.S. Pat. No. 5,403,341 to Solar, relates to stent delivery and deployment assembly which uses a retaining sheath positioned about opposite ends of the compressed state. The retaining sheaths of Solar are adapted to tear under pressure as the stent is radially expanded, thus releasing the stent for engagement with the sheaths. U.S. Pat. No. 5,108,416 to Ryan et al. describes a stent introducer system which uses one or two flexible end caps and annular socket surrounding the balloon to position the stent during introduction to the deployment site. The content of all of these patents is incorporated herein by reference.

In positioning a balloon expandable stent on the delivery catheter over the fluid expandable balloon, the stent must be smoothly and evenly crimped to closely conform to the overall profile of the catheter and the unexpanded balloon. It has been noted that, due to physical properties of the material used in manufacturing the stent (typically a shaped memory metal, such as stainless steel or Nitinol™) there is a certain amount of "recoil" of the stent despite the most careful and firm crimping. That is the stent evidences a tendency to slightly open up from the fully crimped position and once the crimping force has been released. For example, in the typical stent delivery and deployment assembly, if the stent has been fully crimped to a diameter of approximately 0.0035", the stent has been observed to open up or recoil to approximately 0.0037". This phenomenon has been characterized as "recoil crimping". Due to recoil crimping to this slightly enlarged diameter, it can be understood that the stent tends to evidence a certain amount of looseness from its desired close adherence to the overall profile of the underlying catheter and balloon. That is, the stent tends to have a perceptible relatively slack fit in its mounted and crimped position. During delivery, the stent can thus tend to slip and dislocate from its desired position on the catheter or even become separate from the catheter, requiring further intervention by the physician.

According to the present invention, a securement device is secured over the inner catheter beneath the balloon to compensate for the undesired looseness or slack that due to recoil crimping and to aid in securing the stent to the balloon, as well as protecting the balloon material from being sandwiched between the stent and any metal or protruding item which may be mounted on the inner shaft/ guide wire lumen, for delivery of the stent. The securement devices secure the stent during tracking and delivery and provide a good friction fit to the stent and insure good contact between the stent and underlying balloon and catheter, instead of merely crimping the stent onto the balloon and the underlying catheter and relying on the bulk of the flaccid balloon to hold the stent on.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

SUMMARY OF THE INVENTION

This invention concerns a catheter apparatus suitable for performing angioplasty and for delivery of stents to body cavities. In general, stents are prosthetic devices which can be positioned within a body cavity, for example, a blood vessel or in some other difficultly accessible place of the body of a living human or animal. The stent prosthesis is formed of a generally tubular body, the diameter of which can be decreased or increased. Stents are particularly useful for permanently widening a vessel which is either in a narrowed state, or internally supporting a vessel damaged by an aneurysm. Such stents are typically introduced into the body cavity by use of a catheter. The catheter is usually of the balloon catheter type in which the balloon is utilized to expand the stent, which is positioned over the balloon for delivery, to place it in a selected location in the body cavity. The present invention is particularly directed to improved arrangements for releasably attaching and securing the stent to the catheter to facilitate delivery thereof, specifically having a securement device within the balloon. The below identified embodiments all disclose improved means for securing the stent to the catheter during the delivery procedure.

In certain embodiments the stent is held in place on the catheter by means of an enlarged mounting body carried within the balloon by the catheter shaft to which the stent and balloon are fitted. The stent is fitted over the balloon, as by crimping. According to the invention in some embodiments, the enlarged body is axially movable on the inner shaft of the catheter so that it can be retracted from the stent mounting area to provide a small profile for performing angioplasty. The catheter can then be withdrawn; the enlarged body can be moved into the stent mounting area; the stent can be mounted and the catheter can be re-inserted to implant the stent. In other embodiments, the enlarged body can be arranged to be reducible and enlargeable in size rather than being movable. Alternatively, the movable mounting body may be carried outside the balloon. A catheter of this type makes possible a method in which, before stent loading with the associated mounting body arranged to provide reduced diameter in the balloon region, the catheter may be used to dilate a lesion or the like. The catheter may be withdrawn and the mounting body may then be selectively manipulated to provide an enlarged diameter in the stent mounting region and a stent may be loaded onto the catheter. The catheter may be re-inserted to implant the stent. The catheter may be withdrawn or left in situ and the mounting body may be manipulated to provide reduced diameter again and the catheter may be used for any post-dilation desired. Also, the catheter may be used multiple times in the procedure for dilation and stent implantation.

Another embodiment of the present invention is also an assembly for delivery and deployment of an inflation expandable stent within a vessel. The assembly comprises a catheter, an expandable tube component mounted on the catheter, an expandable balloon mounted on the catheter and encompassing the tube component, and a stent mounted on the balloon. The catheter has proximal and distal ends. The stent is inflation expandable from a delivery diameter to a deployment diameter. The delivery diameter is reduced from the deployment diameter for conforming the stent to the catheter. The stent, in its delivery diameter, is coaxially mounted on the catheter near the catheter distal end. The expandable balloon is coaxially mounted on the catheter axially within the stent. The balloon is designed and adapted for expansion of the stent from the delivery diameter to the deployment diameter upon application of fluid deployment pressure to the balloon. The expandable tube component is coaxially mounted on the catheter, axially within the expandable balloon. The tube components is designed and adapted for fluid expansion to provide a securement pressure to the stent in the delivery diameter to maintain the stent in position on the catheter during delivery to the deployment site. The expandable tube component is sized and constructed to be fluid expandable to no more than the delivery diameter. The tube component is essentially equal in length to the stent and the stent is positioned on the assembly essentially coextensive with the tube component.

In another embodiment, this invention is a method for delivering and deploying a stent using an assembly as just described. A catheter is provided having proximal and distal ends. An expandable balloon is coaxially mounted on the catheter. An expandable tube component is coaxially mounted on the catheter, axially within the expandable balloon. The balloon and the tube component are each in an unexpanded condition. A stent is provided which is expandable from a delivery diameter to a deployment diameter. The stent, in a diameter greater than the delivery diameter, is mounted on the balloon. The stent is collapsed to the delivery diameter to conform to an overall profile of the catheter, the tube component and the balloon. The tube component is inflated to provide to the stent a securement pressure, to retain the stent on the assembly in the delivery diameter. The assembly is delivered to a deployment site. The balloon is inflated to expand the stent to its deployment diameter.

An alternative embodiment of present invention is also an assembly for delivery and deployment of an inflation expandable stent within a vessel. The assembly comprises a catheter, an expandable balloon mounted on the catheter, a corrugated tubing mounted on the catheter beneath or within the balloon, and a stent mounted on the balloon. The catheter has proximal and distal ends. The stent is inflation expandable from a delivery diameter to a deployment diameter. The delivery diameter is reduced from the deployment diameter for conforming the stent to the catheter. The stent, in its delivery diameter, is coaxially mounted on the catheter near the catheter distal end. The expandable balloon is coaxially mounted on the catheter axially within the stent. The balloon is designed and adapted for expansion of the stent from the delivery diameter to the deployment diameter upon application of fluid deployment pressure to the balloon. The corrugated tubing is mounted and adhered coaxially onto the catheter and is situated between the balloon and the catheter itself. When the stent is crimped and loaded onto the balloon, the balloon is situated therefore between the stent and the corrugated tubing. The tubing is preferably essentially equal to the length of the stent and the stent is positioned on the assembly essentially co-extensive with the tube component. The tubing on the catheter effectively holds the stent in place, takes up the slack due to recoil and protects the balloon material from being damaged during crimping.

Still another embodiment of the present invention comprises an assembly for delivery and deployment of an inflation expandable stent. The assembly comprises a catheter having proximal and distal ends. An annular collar or the like is coaxially located on the catheter distal end. A fluid expandable balloon is coaxially mounted over the collar at the catheter distal end. The balloon is expandable from a contracted to an expanded state. A stent is coaxially mounted on the balloon. The stent is inflation expandable from a reduced to an enlarged condition, the reduced condition conforming the stent to the balloon, collar and catheter in the preferred embodiment. The stent has at least an end portion overlying the balloon. At least one cup is coaxially mounted on the catheter distal end. The cup has a first end portion which may overlie the stent end portion. The cup and collar are cooperatively constructed and arranged to retain the stent end portion on the catheter in the stent reduced condition when the balloon is in the contracted state. The balloon and catheter are cooperatively constructed and arranged to cause expansion of the balloon from the contracted to the expanded state to cause enlargement of the stent, including the stent end portion, from the reduced to the enlarged condition, and thereby release the stent end portion from the cup end portion. The cup may be axially spaced from the collar but preferably they are relatively close together. The second end portion of the cup may be fixed to the catheter. The cup may overlie at least a portion of the collar. The collar can be shaped as a single member with the catheter, that is integral with it or the collar may be a separate body mounted axially and positioned on the catheter. The collar may be a mounting ring or cylinder axially positioned between stent end portions under the stent and balloon. The collar may be a sheath under the stent and balloon.

A further embodiment is also directed to improved arrangements for releasably attaching the stent to the catheter to facilitate delivery thereof. The stent is held in place on the catheter by means of an enlarged body carried by the catheter shaft within the balloon to which the stent and balloon are fitted, as by crimping in combination with one or more sleeves releasably overlying an end portion or portions of a stent and balloon.

BRIEF DESCRIPTION OF THE FIGURES

FIG. 1 is an isometric view, a portion of which is enlarged and in longitudinal section, of a balloon catheter having a mounting body in a retracted position;

FIG. 2 is an even more enlarged view in longitudinal cross-section of the distal end portion of the catheter of FIG. 1;

FIG. 3 is similar to FIG. 2 but showing the mounting body advanced to receive a stent mounted on the balloon;

FIG. 4 is an enlarged cross-sectional view of the distal end portion of the catheter of FIG. 1 similar to that of enlarged view FIG. 3 but showing the balloon in an expanded condition along with the expanded stent;

FIG. 5 is a schematic showing of a preferred mounting body carried by the catheter shaft within the balloon, the body being spirally cut to improve flexibility;

FIG. 6 is a schematic showing in cross-section of another embodiment of the invention with a mounting body positioned to receive a stent but with a stent not yet mounted;

FIG. 7 is a schematic showing of another embodiment of the invention;

FIG. 10 is a showing of another embodiment of a mounting body according to the invention;

FIG. 11 is a schematic of an enlargeable mounting body which is not axially movable;

FIG. 12 is a schematic of an alternate enlargeable mounting arrangement which is not axially movable;

FIGS. 13 and 14 are schematic showings of yet another embodiment in which the axially movable mounting body is carried outside the balloon;

FIGS. 15 and 16 are schematic showings of still yet another embodiment of the invention.

FIGS. 19–21 are modified versions of the securement means of the present invention.

FIG. 22 is a side profile section showing a balloon expandable stent delivery and deployment assembly, with the stent crimped to delivery diameter onto the balloon, the underlying inflating component and the catheter and with the inflating tube component inflated to securement pressure.

FIG. 23 is a side profile section, similar to FIG. 22, with the balloon and the stent fully inflated to deployment diameter.

FIG. 24 is a side profile section showing an alternative embodiment of a balloon expandable stent delivery and deployment assembly, having a tube component formed in several sections.

FIGS. 25, 26 and 27 are cross-sectional views taken along lines 4—4, 5—5 and 6—6 of FIG. 24, respectively.

DESCRIPTION OF THE PREFERRED EMBODIMENTS

Figure 8:
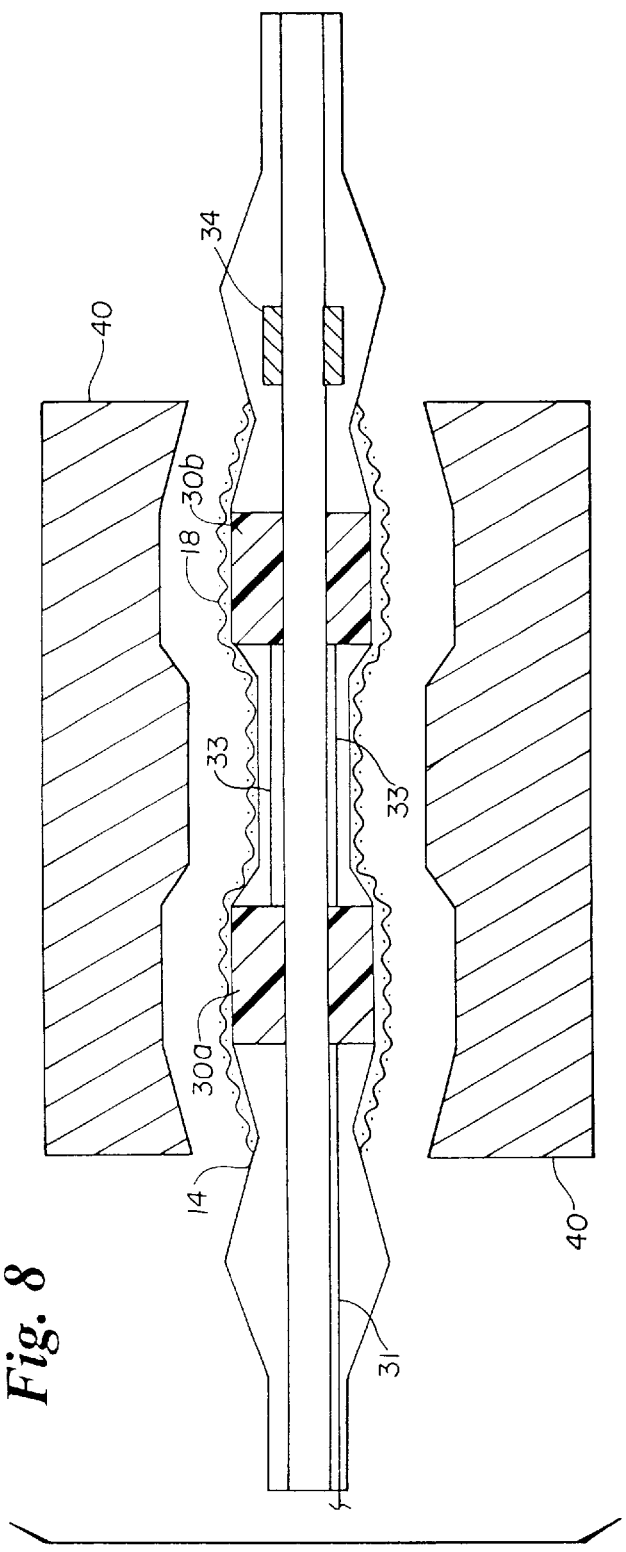
FIG. 8 is a schematic showing of a means for conveniently crimping the stent on the embodiment shown in FIG. 5.

The present invention relates to stent securement devices, most notably positioned between the balloon and the inner shaft of the catheter. Individual elements of the below disclosed embodiments are generally interchangeable if desired. Referring to FIGS. 1–4 an angioplasty and stent delivery catheter system generally indicated at 10 includes a balloon catheter 12 having a balloon 14 on a distal end portion generally indicated at 16. FIG. 1 shows a proximal portion of the catheter at 12a and a distal portion 12b in enlarged view. FIGS. 2 and 3 show the distal end portion 16 in an even more enlarged view. The illustrative catheter 12 is of the type known as a rapid exchange or single operator catheter. However, other types of catheters may be used, such as over the wire and fixed wire types. The balloon 14 is fixed to the catheter 12 by standard means. The balloon is shown in its contracted state in. A stent 18 is fixed about the balloon by crimping thereto. The stent has a larger expanded diameter which is obtained when the balloon is expanded in the known manner. In FIGS. 1 and 2 catheter is shown prepared for performing angioplasty and in FIG. 3 it is prepared for stent implantation.

In FIGS. 1 and 2, an axially movable mounting body 30 is shown in a position proximal to the end portion 16 of the catheter where a stent may be mounted. The catheter includes at its proximal end a manifold, generally designated 13, as is known in the art. The manifold includes an inflation port 15 as is known in the art. A wire 31 is attached to body 30 to enable remote (from the proximal catheter end) advancement and retraction of it axially on inner lumen 26 over which it slides. In the retracted position shown in FIGS. 1 and 2, the catheter has a low profile for performing angioplasty.

This position is a retracted position and is selected by operation of a pull wire 31. The retracted position of the mounting body may vary. To maximize the low profile of the distal end 16 of the catheter, the retracted position may be within the outer member 24.

After such a procedure, the balloon is deflated, the catheter is withdrawn and the mounting body is advanced by means of wire 31 to the stent mounting position shown in FIG. 3. A stent 18 may then be fixed about the deflated balloon by crimping it thereto. The stent has a larger expanded diameter which is obtained when the balloon is again expanded in the known manner. That is, the stent is released from the catheter upon expansion of the balloon as shown in FIG. 4 to be placed in a vessel at the desired location. When the balloon is then again deflated, removal of the balloon and catheter may be accomplished, leaving the stent in place. Exemplary dimensions for the inner 26 is a diameter of ½ mm and for body 30 a diameter of ¾ mm.

As is known in the art the balloon is either bonded at its ends by adhesive 20 and 22, respectively to the outer member 24 of the catheter and to the inner member 26 of the catheter in the manner as shown, or is made one-piece with the outer member as is known in the art. The catheter balloon may be inflated by fluid (gas or liquid) from an inflation port extending from a lumen 28 (seen in FIGS. 2 and 3) contained in the catheter shaft and opening into the balloon as shown, or by other known arrangements, depending on the design of the catheter. The details and mechanics of balloon inflation and specific overall catheter construction will vary according to the particular design involved in any given instance, and are known in the art per se. Such details are only shown schematically herein. All variations are acceptable for use with this invention.

Any balloon expandable stent may be used with this invention. Many are known in the art including plastic and metal stents. Some are more well known such as the stainless steel stent shown in U.S. Pat. No. 4,735,665; the wire stent shown in U.S. Pat. No. 4,950,227; another metal stent shown in European Patent Application EPO 707 837 A1 and that shown in U.S. Pat. No. 5,445,646, or U.S. Pat. No. 5,242,451. All of these patents are incorporated herein by reference. Also, shape memory metal stents may be used. As already indicated the stent of PCT Application 960 3092 A1 is particularly preferred.

The stent is typically for example about 16 mm long, while the balloon may be 20 mm long for example. These dimensions, however, are merely representative for illustrative purposes only and are not meant to be limiting. The stent is positioned over the balloon portion of the dilatation catheter and gently crimped onto the balloon either by hand or with a tool such as a pliers or the like to be mounted for delivery as shown in FIG. 3. The crimping may be readily accomplished by the physician during the procedure.

In accordance with this invention, mounting body 30, best seen in FIGS. 2 and 3, is included inside balloon 14 to provide a cushion and/or substrate of enlarged diameter relative to the stent to support and hold the stent and secure it during crimping and the delivery procedure. The mounting body may be axially movable proximally or distally from the position shown in FIG. 3, proximally being preferred.

In the embodiment shown in FIGS. 1–3, mounting body 30 is cylindrical in form and takes the shape of a sleeve axially and slidably carried on inner lumen 26, providing an enlarged area or portion for receiving the balloon and stent when the latter is crimped to the balloon. Marker band 34 may also be included on inner 26 as shown. Any radiopaque material such as gold is useful for this purpose. A stop member 36 of generally conical shape or any other shape may also be included on the marker band 34 as shown to provide additional resistance to stent movement during delivery and to protect the leading edge of the stent during delivery. Polyethylene or the like is suitable for the stop member. Other marker arrangements and stop arrangements may be used as well.

Although, the material of the mounting body may be hard, it is preferably of any deformable thermoplastic material, preferably an elastomer material and more preferably of a relatively resilient elastomer material, e.g., lower durometer silicone. A preferred deformable thermoplastic material is high density polyethylene (HDPE). A preferred lower durometer silicone is in the form of tubing. The deformation of the resilient material of the mounting body when the stent/balloon is crimped to it causes a radial outward force on the stent/balloon increasing the friction therebetween despite any recoil of the stent.

During stent delivery, the balloon catheter is advanced through and positioned in a patient's vasculature so that the stent is adjacent to the portion of the vessel where treatment is to take place. The balloon is inflated to expand the stent to an enlarged diameter. When the stent has reached the desired diameter, the balloon is deflated so that the catheter may be removed leaving the stent in place.

Another embodiment of the invention is shown in FIG. 5. In this embodiment mounting body 30 is a spiral cut elastomer or other suitable material, such as a rigid or flexible plastic, to provide separation for flexibility in that portion of the catheter, allowing more easy movement or tracking around bends. The spiral cut may be only partly through the mounting body or may be all the way through as shown in FIG. 5. Also, while stop member 36 is shown at the distal end portion of the catheter in this embodiment, no stop member may be used.

Another similar version is shown in FIG. 6 which includes a cylindrical mounting body 30 made up of a plurality of separate adjacent rings 30*a* held together by wire 31 which extends therethrough as shown with stops 29 to secure the rings together. Rings 30*a* may be individual bodies carried on the sheath or bodies cut from a cylinder to partially separate them or fully separate them. Suitable arrangements may be made to wire 31 at each end of the body 30 to hold the rings together, as shown.

The embodiment shown in FIG. 7 includes another feature based on the geometry of the mounting body for further securing the stent upon crimping. This feature is referred to herein as "interlocking". That is, the stent may be interlocked to the mount so that the stent cannot slide proximally or distally on the balloon unless it is deformed, such as by expansion. This can be seen by perusing the structure shown in FIG. 7 which includes the inner 26 having a two-piece mounting body made up of spaced mounting bodies 30*a* and 30*b*. These bodies are connected to each other by connection means 33 which may be a separate or integral cylindrical body of lesser diameter or may be one or two or more relatively rigid wire members as shown. The spacing between bodies 30*a* and 30*b* allows portions of the stent 18 and balloon 14 to be depressed or inserted between the bodies upon crimping of the stent thus forming an interlock against sliding of the stent axially or longitudinally before the stent is released.

The interlock formation or crimping is readily accomplished by any suitable means such as a two-piece die 40 shown in FIG. 8 or the like.

Figure 9:
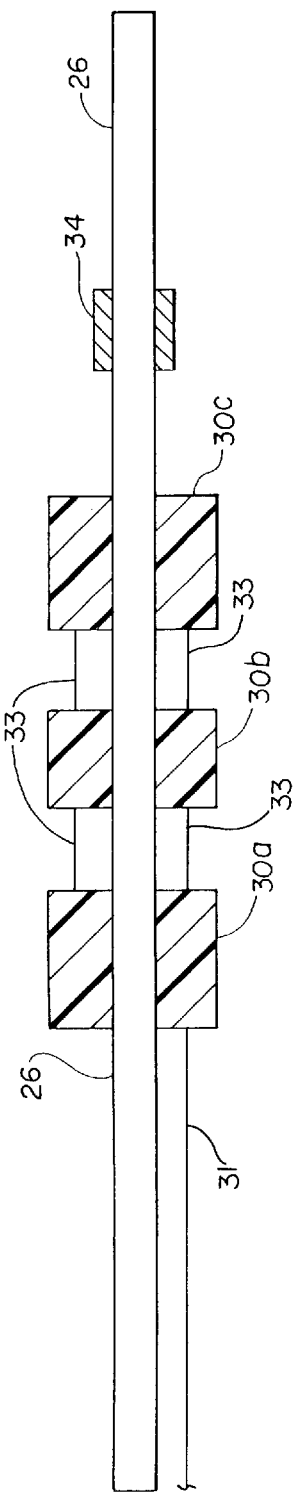
FIG. 9 is a schematic showing of yet another embodiment of the invention.

FIG. 9 demonstrates that more than a two-piece mounting body arrangement may be used if desired. In this embodiment, the mounting body is comprised of three spaced interconnected bodies 30*a*, 30*b* and 30*c* on the inner 26. Preferably in the embodiments of FIGS. 7 and 9, the mounting bodies will be ring-like in shape or cylindrical in shape although other configurations will be readily apparent to those familiar with this art.

Referring now to FIG. 10, another embodiment of a movable mounting body 30 is shown in the form of a rigid coil of plastic, metal or the like having a control wire 31, preferably integral therewith. When in the metal form, the coil may be coated with a polymer such as polyethylene or PTFE or enclosed in a polymeric sheath of similar material. The coil may be slidably received on the inner 26 similar in arrangement to that shown in the preceding Figures.

As already indicated, an alternate arrangement may be used in which the mounting body, instead of being movable, is designed to be enlargeable and reducible or collapsible, while remaining in a fixed position in the stent mounting area of the catheter. FIGS. 11 and 12 are directed to such an arrangement.

In FIG. 11, an inner balloon 50 of smaller diameter than outer balloon 14 is mounted on the inner 26. Balloon 50 may have a separate inflation conduit 52 inside inner 26, preferably including a valving arrangement 54. Valve 54 may be a one-way valve allowing only inflation of balloon 50 if desired. However, inner 26 may serve as the inflation conduit as well. In addition to fully inflating the balloon, inner balloon 50 may also be partially inflated.

FIG. 19 shows a modification to FIG. 11 in which two inner balloons 50a and 50b are included. FIG. 20 shows a modification in which two inflation valves 54a and 54b are included.

FIG. 21 shows a full arrangement of inner balloon 50 in which a syringe 120 is inserted into the distal end of the liner 26 of the catheter. The syringe has at its ends blocks 122 and 124 to enable local pressurization of inner 26 to inflate balloon 50.

Figure 17:
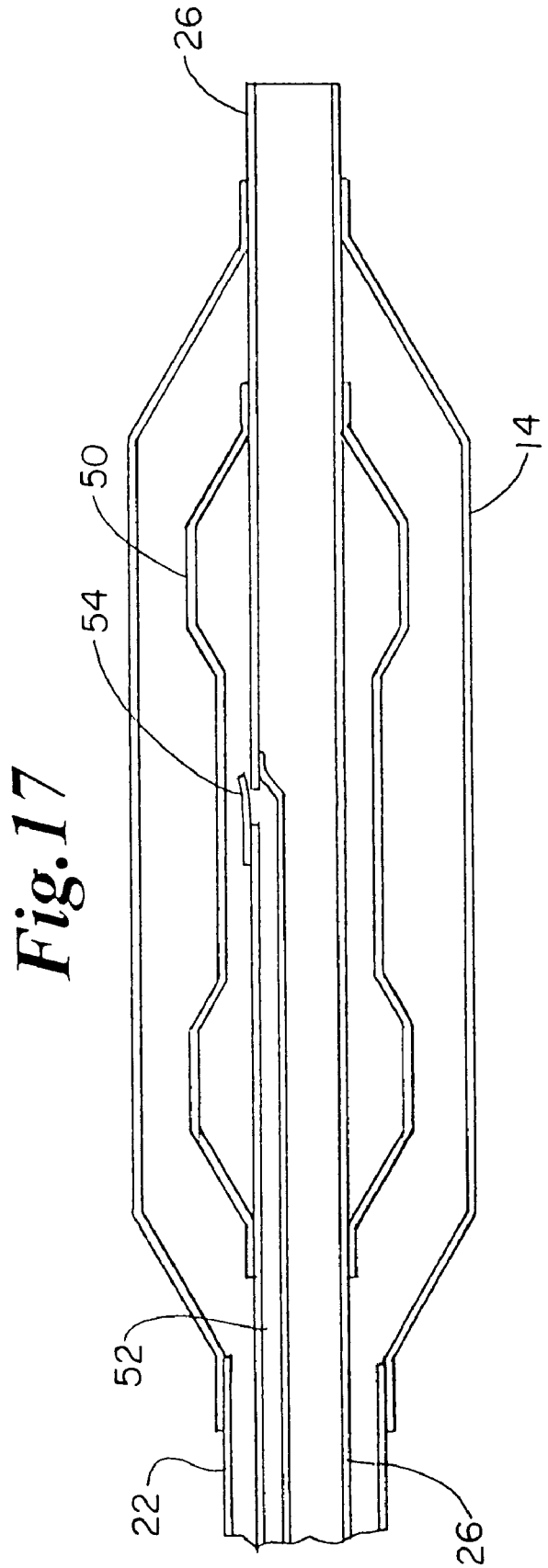
FIGS. 17 and 18 are modified versions of the embodiment shown in FIG. 11.
Figure 18:
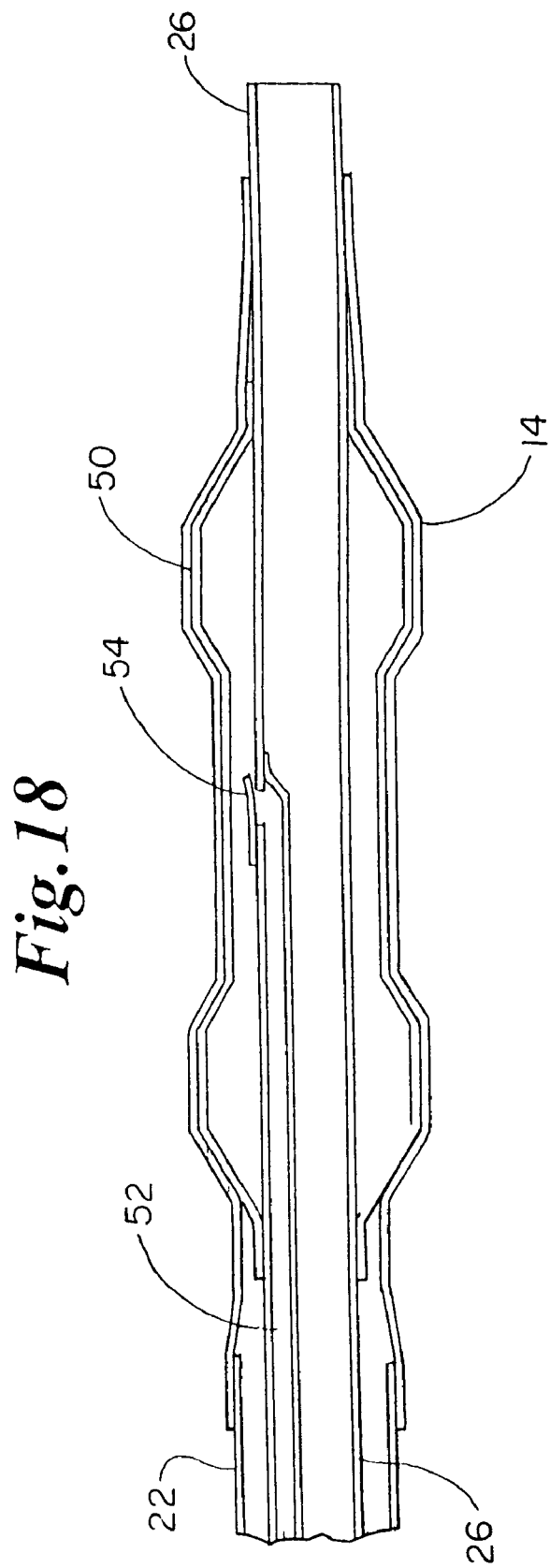

FIGS. 17 and 18 show an inner balloon 50 similar to the arrangement of FIG. 11 but the balloon 50 in FIG. 17 has a narrow center portion and wide ends to provide a mounting shape similar to that of FIG. 7. In FIG. 17, balloon 50 is inflated and balloon 14 is partially inflated. In FIG. 18, balloon 50 is inflated and balloon 14 is uninflated ready for stent loading. Balloon material is preferably a polyethylene or urethane elastomer such as Tecoflex or Tecothane from Thermedics.

Referring to FIG. 12, an alternate embodiment is shown in which the proximal portion of the inner 26 is axially movable while the distal portion 26b is fixed with respect to the catheter. In between portion 26a and portion 26b is a coil spring 60 inside a flexible sheath 62 of PTFE or the like. Portion 26b of the inner is attached to balloon 14 at the very distal end portion of the catheter. Portion 26a is movable axially within the outer 22. Thus, if 26a is pushed in the distal direction and held to compress coil 60, the coil will enlarge in diameter to provide an enlarged mounting area for a stent. Twisting the inner to twist the coil will enhance enlargement. Alternatively, coil spring 60 may be replaced by a braided element.

Also, by providing different pitch over the length of the coil it can be made to enlarge more in some regions than in others. For example, if the coil windings are closer together in the center portions than in the end portions, when the coil undergoes compressing, the two end portions will enlarge in diameter more than the center portion to provide a mount similar to that of FIG. 7.

Referring now to FIGS. 13 and 14, another embodiment is shown which is alternative to the earlier described embodiments which are inside the balloon on the catheter. In this embodiment a sheath 80 is carried on the outside of the catheter. Sheath 80 is elastomeric and is axially movable from a stent mounting position as shown in FIG. 14 to a position remote from the stent mounting position, such as the retracted position as shown in FIG. 13. In the position shown in FIG. 13, balloon 14 may be inflated and deflated. In the position shown in FIG. 14, balloon 14 will be deflated for low profile. Sheath 80 when over the balloon as in FIG. 14 acts to increase the profile of the catheter to facilitate crimping a stent thereto during deployment of the stent, sheath 80 will expand with balloon 14 to facilitate inflation and during deflation the elastomer sheath will return to its original dimension. An elastomer material which is presently preferred is Tecothane, a trade name for a thermoplastic polyurethane available from Thermedics, Inc., of Woburn, Mass. It may be about 0.003 inches thick, for example.

With respect to FIGS. 15 and 16, a further embodiment of the invention is shown in which inner 26 carries a mounting body 30, the distal end 100 of which is secured or fixably attached to inner 26, as by any suitable adhesive. The remainder of body 30 is slidable over inner 26 as by the application of compression in the distal direction at the proximal end 102. This may be accomplished by push wire 104 which extends to the proximal end of the catheter for remote manipulation as is known in the art.

Mounting body 30 is accordion folded with more widely spaced folds at the end portions 106, than at the central portion 108. Thus, as can be seen in FIG. 15, a relatively low profile is provided without compression for normal angioplasty use. When a stent is to be mounted (not shown), compression by means of push wire 104 will result in a configuration of enlarged diameter of body 30 as shown in FIG. 16 to provide a mount similar to that of FIG. 7 in general configuration. If the spring is uniform over the body, it sill enlarge uniformly, similar to the inner balloon of FIG. 11. The Figures are schematic in form but the concept can be readily appreciated.

As an alternative to a folded construction, the body may be of braided construction to achieve the same operation.

Also, this form of body 30 may be inserted into a two piece inner 26 similar to the arrangement shown in FIG. 12. In all of these arrangements, the accordion folded body material may be of any suitable polymer, such as polyethylene. For example, tubing having a wall thickness of about 0.002 inches may be used. The accordion folds or pleats may be readily formed in such tubing by means of a pressure mold containing spaced blades placed in a heated chamber.

FIGS. 22–27 show embodiments wherein the inner securement device comprises an inner balloon beneath the outer catheter balloon, similar to above. FIGS. 22 and 23 illustrate a side profile section showing an inflation expandable stent delivery and deployment assembly generally designated 110. Assembly 110 includes a catheter comprised of inner shafts 112 and 113 and an outer shaft 115 of the coaxial type, an inflation expandable balloon 114, an inflation tube component 116 such as an inner balloon and inflation expandable stent 118. Any conventional type of catheter may be used, such as a catheter of the type generally used for PTA or PTCA angioplasty procedures, for prostate therapy, and TTS endoscopic catheters for gastrointestinal use. However, coaxial types as shown are most preferred. The particular catheter 112 shown is formed of a biocompatible and hydrophilic compatible material, such as a lubricous polyimide or polyethylene. Other suitable materials for the catheter 112 include nylons, urethanes, and polypropylene materials compatible with coatings such as silicone and/or hydrophilic coatings. In addition to hydrophilic compatible materials, any biocompatible material may be used. For example, polyethylene or polypropylene can be coated with a hydrophilic material to render them hydrophilic compatible suitable catheters for use according to the present invention include a number of catheters available from SciMed Life Systems, Inc., Maple Grove, Minn., the assignee of the present invention, such as BANDIT™, COBRA™, VIVA™, and VIVA PRIMO™ catheters.

Inflatable tube component 116 is fixed at its distal and proximal end to inner shaft 112 and at its proximal end to inner shaft 113 at a position to be encompassed within the distal and proximal ends of the outer balloon 114. According to art-recognized convention, the length L-B of the balloon 114 is defined as the length of the body portion of the balloon 114, excluding the terminal cone sections 120. As seen in FIG. 23, the body portion of the balloon 114 is generally cylindrical when in its deployed or inflated condition. Tube component 116 is illustrated as having terminal sections 122 which are more relatively vertical than the cone sections 120 illustrated for the balloon 114. However, it is to be understood that, according to the present invention, either of the terminal sections 120, 122 may be relatively cone shaped, relatively vertical or of any other configuration known to those of skill in this art. A preferred length L-T of the tube component 116 is illustrated in FIGS. 22 and 23 as substantially equal to the length L-B of balloon 114, and substantially equal to the length L-S of stent 112. However, according to the present invention, stent 112 should be supported by the underlying tube component 116 for a length sufficient to permit accomplishment of the stated purpose of the tube component 116, when inflated, to provide securement pressure for stent 112 to maintain stent 112 in position with assembly 110 during delivery. It is also within the present invention for tube component 116 to be slightly shorter than stent 112, for example, the distal end 119 of stent 112 may extend distally beyond the distal end 121 of tube component 116 (not shown), so that the distal end 119 of stent 121 can be crimped over the distal end 121 of tube component 116 to prevent the distal end 119 of stent 112 from catching and tending to further open as it is maneuvered within a body vessel. As has been explained above, tube component 116 is designed and constructed to be inflatable to no more than is necessary to compensate for recoil crimping of stent 112 and to closely accommodate (or even slightly over-stress) the delivery diameter of stent 112, taking into consideration the thickness of the intervening uninflated balloon 114. Tube component 116 is inflated through the opening(s) 117 of inner shaft 112. Typically, tube component 116 will have a wall thickness of about 0.0002–0.0007 inch and will be inflatable to no more than about 0.035.–0.045 inches.

Inflating tube component 116 may be formed of either compliant or non-compliant balloon materials. Compliant materials include low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyether-polyamide copolymers. Suitable materials include a copolymer polyolefin material available from E. I. DuPont de Nemours and Co. (Wilmington, Del.), under the trade name Surlyn™ Ionomer and a polyether block amide available under the trade name PEBAX™. Non-compliant materials include relatively rigid of stiff high pressure polymeric materials, such as thermoplastic polymers and thermoset polymeric materials, poly(ethylene terephthalate) (commonly referred to as PET), polyimide, thermoplastic polyimide, polyamides, polyesters, polycarbonates, polyphenylene sulfides, polypropylene and rigid polyurethanes.

A balloon 114 for use according to the present invention may be any conventional balloon for catheter delivery, such as a balloon of the type generally used for PTA and PTCA procedures. Typically, balloon 114 is fixed at its distal end to inner shaft 112 near the catheter distal end and at its proximal end to outer shaft 115. Balloon 114 is larger in diameter than tube component 116, because balloon 114 must be able to expand to a larger diameter than tube component 116. Balloon 114 is inflatable through an inflation conduit 123, i.e., the space between coaxial inner shaft 113 and outer shaft 115 of the catheter. The distal and proximal ends of balloon 114 are shown in FIGS. 22 and 23 positioned exterior to the distal and proximal ends of tube component 116, respectively, and of a length L-B generally equal to the length L-T of the tube component 116. To be compatible with tube component 116 illustrated in FIGS. 22 and 23 and described above, balloon 114 is inflatable at deployment to about the diameter of the body vessel in which the stent 118 is to be deployed. Balloon 114 may be formed of a compliant or non-compliant material, of the types of compliant materials described herein above, such as polyethylene or any standard balloon material. Balloon 114 typically has a wall thickness of about 0.0007–0.004 inch for example.

A stent for use according to the present invention may be any conventional type of balloon expandable stent, including stents of the type used for PTA and PTCA angioplasty procedures, for prostate therapy, and TTS endoscopic catheters for gastrointestinal use. Suitable stent material is biocompatible stainless steel in the form of sheet metal, tube component wire or Nitinol. A preferred stent is described in PCT Application No. 960 3072 A1, published Feb. 8, 1996, the content of which is incorporated herein by reference. All such stents are well known in this art generally and additional examples are described in U.S. Pat. No. 5,507,768 to Lau et al.; in U.S. Pat. No. 5,458,615 to Klemm et al; in U.S. Pat. No. 5,226,889 to Sheiban; in U.S. Pat. No. 4,875,480 to Imbert; in U.S. Pat. No. 4,848,343 to Wallsten et al., and in U.S. Pat. No. 4,733,665 to Palmaz. Stent 18 as shown in FIGS. 22 and 23 is positioned on balloon 114, the underlying inflatable tube component 116 and the distal end of the catheter. The length L-S of stent 118 is shown as essentially equal or slightly smaller than the length L-T of tube component 116 and is positioned on assembly 110 to be co-extensive with tube component 116. In this position, stent 118 is shown in FIG. 22 crimped to its delivery diameter D1, which is about 0.035–0.045 inch for example.

As discussed above, despite the most careful and firm crimping of stent 118 to closely conform to the overall profile of the catheter unexpanded balloon 114 and underlying inflatable tube component 116, there is a certain amount of "recoil" of stent 118 or a tendency of stent 118 to slightly open from a desired hypothetical minimum crimped diameter. The actual minimum diameter achievable for fully crimped stent 118 on assembly 110 is referred to as the stent 118 delivery diameter D1. This tendency of stent 118 to open or recoil slightly when crimped on assembly 10 has been characterized as "recoil crimping". In FIG. 22, inflatable tube component 116 is shown inflated to a diameter which is generally sufficient to compensate for any slack or looseness between crimped stent 118 and the overall profile of the catheter, the unexpanded balloon 114 and the underlying inflatable tube component 116 due to recoil crimping.

FIG. 23 illustrates a side profile section showing a stent delivery and deployment assembly 110 of this invention with balloon 114 fluid inflated to its fully expanded position. As a result of the fluid inflation of the balloon 114, stent 118 has also been fully expanded to its deployment diameter D2 in which it can be deployed against the walls of a body vessel in which it is situated.

Tube component 116 may have a shape other than the cylindrical shape described and illustrated with regard to the embodiment shown in FIGS. 22 and 23. Further, the tube component may be comprised of more than one separately inflatable pouch. For example, as illustrated with regard to FIG. 24, the tube component of an alternative stent delivery and deployment assembly generally designated 130 can be comprised of three separately inflatable pouches 136, 138, 140. The pouches 136, 138, 140 are each separately inflatable through their respective inflation conduits 137, 139 141, and each of the pouches 136, 138, 140 can be inflatable to a different extent. The conduits are formed in the wall of shaft 132 as can be seen in FIGS. 25–27. The stent delivery and deployment assembly 130 of FIG. 24 is also comprised of a catheter having inner shaft 132 and outer shaft 135, a balloon 134, with its balloon inflation conduit 139 and the balloon terminal cone sections 144, and a stent 142. As has been explained above with reference to FIGS. 22 and 23, stent 142 is crimped to closely conform to the overall profile of the catheter the unexpanded balloon 134 and the underlying inflatable pouches 136, 138, 140. Even with the most careful and firm crimping, there is a certain amount of "recoil" of the stent 142 or a tendency of stent 142 to slightly open from a desired hypothetical minimum diameter. In FIG. 24, the first 136 and third 140 pouches are inflated to a slightly larger size than the second pouch 138. As discussed above, the inflation of the pouches 136, 138, 140 to this configuration is generally sufficient to compensate for any slack or looseness between the crimped stent 142 and the overall profile of the catheter, the unexpanded balloon 134 and the underlying inflatable pouches 136, 138, 140 due to recoil crimping. Once pouches 136, 138 140 have been inflated to the configuration shown in FIG. 24, stent 142 is firmly secured against axial movement with regard to assembly 130. The distal 146 and proximal 148 ends of stent 142 are protected from any possible unwanted contact with vessel walls during maneuvering, which helps to protect the vessel walls from abrasion and also helps to protect the ends 146, 148 of stent 142 from distortion. Additionally, stent 142 may be of a length such that it fits over pouch 140 and pouch 136 as well as over pouch 138.

The method of using the stent delivery and deployment assembly 110 of this invention, as shown in FIGS. 22 and 23, is described as follows. The assembly 110 is constructed as described above. Stent 118 is compressed or crimped onto balloon 114, inflatable tube component 116 and the catheter to a delivery diameter D1. This crimping can be done manually or with the aid of tooling specially designed for the purpose either by the physician or the manufacturer. In the crimped position, stent we closely conforms to the overall profile of balloon 114, inflatable tube component 116 and the catheter except for the slight slack or looseness due to recoil crimping. Tube component 116 is fluid inflated to the extent necessary to compensate for this slack or looseness due to recoil crimping. The pressure of force required to inflate tube component 116 to this extent is also referred to as securement pressure, i.e., the force or pressure needed to secure stent 112 in this position. It is to be noted that, since tube component 116 is designed and constructed to be capable of fully expanding to no more than the size necessary to compensate for recoil crimping, there is no possibility of stent 112 expanding or beginning to open to a larger diameter. Thus, there is no hazard of stent 112 moving out of its position on the catheter during delivery or of becoming separated from the catheter within a body vessel. The catheter distal end is delivered by standard techniques to the deployment site within the body vessel of interest. At this point, stent 112 is positioned as required by the physician and balloon 114 is fluid inflated by standard technique to expand stent 121 to its deployment diameter D2. During this expansion, stent 112 is expanded to fill the body vessel.

Following deployment of stent 112, balloon 114 and optionally, tube component 116 are deflated and the assembly 110 is retracted proximally and withdrawn from the body. If required by the procedure, the site of entry to the body is appropriately closed.

The method of using the stent delivery and deployment assembly 130 of this invention, as shown in FIG. 24, is similarly described. The assembly 130 is constructed as described above. Stent 142 is compressed or crimped to closely conform to the overall profile of balloon 134, inflatable pouches 136, 138, 140 and the catheter except for the slight slack or looseness due to recoil crimping. Pouches 136, 138, 140 are each fluid inflated to the profile shown in FIG. 24 through separate fluid inflation conduits (not shown) to securement pressure to compensate for this slack or looseness and to secure stent 142 in this position. The overall configuration of pouches 136, 138 140 further serves to position stent 142 against axial dislocation during delivery. The catheter is delivered by standard techniques to the deployment site within the body vessel of interest. At this point, stent 142 is positioned as required by the physician and balloon 134 is fluid inflated by standard technique to expand and deploy stent 142. Following deployment of stent 142, balloon 134 and, optionally, pouches 136, 138 140 are deflated and the assembly 130 is retracted proximally and withdrawn form the body. If required by the procedure, the site of entry to the body is appropriately closed.

The inflation tube component provided by this invention maximizes stent securement force by optimizing the frictional force between the inflating tube component, the balloon wall and the internal diameter of the stent in its reduced crimped delivery diameter. The inflation tube component is more flexible than a solid sheath under the expandable balloon, and thus the entire assembly has greater flexibility. This invention has particular advantages for assemblies in which the stent is provided for use as pre-crimped to the balloon and underlying catheter, by increasing the shelf life of the pre-crimped assembly. The features and principles described for this invention are suitable for use with fixed wire, over-the-wire and single operator exchange assemblies.

Figure 28:
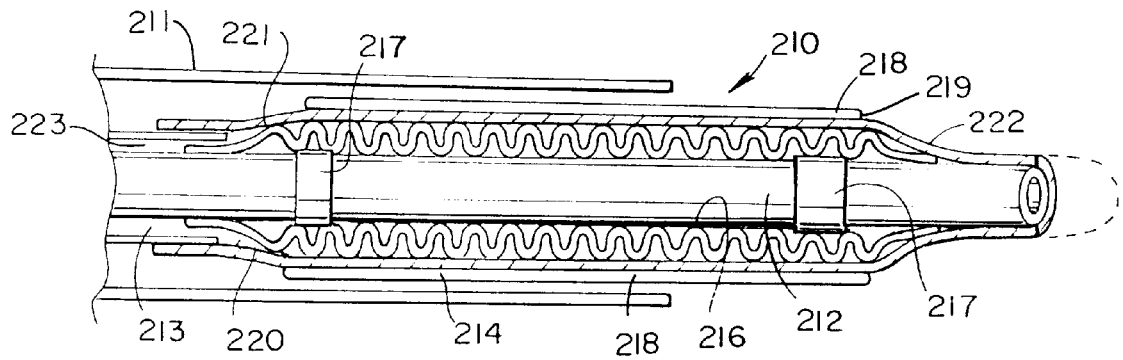
FIG. 28 is a side profile section showing a balloon expandable stent delivery and deployment assembly, with the stent crimped to delivery diameter onto the balloon, the underlying tube component and the catheter.
Figure 29:
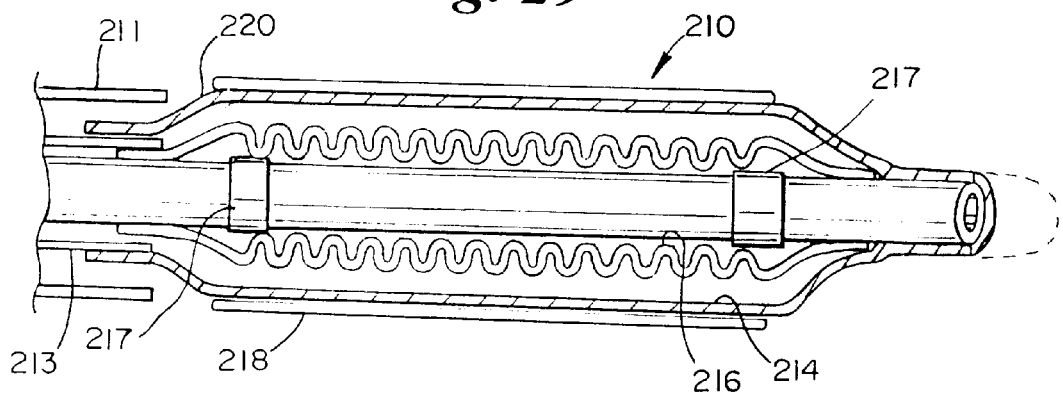
FIG. 29 is a side profile section, similar to FIG. 28, with the balloon and the stent fully inflated to deployment diameter.

FIGS. 28–37 disclose still further embodiments of the securement device. FIGS. 28 and 29 illustrate a side profile section showing an inflation expandable stent delivery and deployment assembly, generally designated 210. Assembly 210 includes a catheter comprised of inner shaft 212 and outer shaft 213 of the coaxial type and an optional retractable delivery shaft 211 (typically called a guide catheter, shown retracted in FIG. 29, an inflation expandable balloon 214, a corrugated/ribbed stent securement device 216, optional marker bands 217 and an inflation expandable stent 218. Any conventional type of catheter may be used, such as a catheter of the type generally used for PTA or PTCA angioplasty procedures, for prostate therapy, and TTS endoscopic catheters for gastrointestinal use. However, coaxial types as show are most preferred. The particular catheters 212 and 213 shown are formed of a biocompatible and hydrophilic compatible material, such as a lubricous polyimide or poly ethylene. Other suitable materials for the catheters 212 and 213 include nylons, urethanes, and polypropylene materials compatible with coatings such as silicone and/or hydrophilic coatings. In addition to hydrophilic compatible materials, any biocompatible material may be used. For example, polyethylene or polypropylene can be coated with a hydrophilic material to render them hydrophilic compatible. Suitable catheters for use according to the present invention include a number of catheters available from SciMed Life Systems, Inc., Maple Grove, Minn., the assignee of the present invention, such as BANDIT™, COBRA™, VIVA™, VIVA PRIMO™, MAXXUM™, MAXXUM ENERGY™ and RANGER™ catheters.

Securement device 216 is fixed at its distal and/or proximal ends to inner shaft 212 at a position to be encompassed within the distal and proximal ends of the outer balloon 214. According to art-recognized convention, the length L-B of the balloon 214 is defined as the length of the body portion of the balloon 214, excluding the terminal cone sections 220. As seen in FIG. 29, the body portion of the balloon 214 is generally cylindrical when in its deployed or inflated condition. Securement device/tube component 16 is illustrated as having terminal sections 221,222. It is to be understood that, according to the present invention, either of the terminal sections 220, 222 may be relatively cone shaped, relatively vertical, relatively flat or of any other configuration known to those of skill in this art. A preferred length L-T of the tubing 216 is illustrated in FIGS. 28 and 29 as substantially equal to the length L-B of balloon 214, and substantially equal to the length L-S of stent 218. However, according to the present invention, stent 218 should be supported by the underlying tube component 216 for a length sufficient to permit accomplishment of the stated purpose of the tube component 216, to provide a superior securement and protective surface for stent 218 to maintain stent 218 in position with assembly 210 and to protect the balloon material during loading/crimping. It is also within the present invention for the tube component 216 to be slightly shorter than stent 218, for example, the distal end 219 of stent 218 may extend distally beyond the distal end 21 of tube component 216 (not shown), so that the distal end 19 of stent 18 can be crimped over the distal end 221 of tube component 216 to prevent the distal end 221 of stent 218 from catching and tending to snag or further open as it is maneuvered within a body vessel. As has been explained above, tube component 216 is designed and constructed to have enough flexibility and have enough volume to no more than is necessary to compensate for recoil crimping of stent 218 and to closely accommodate (or even slightly over stress) the delivery diameter of stent 218, taking into consideration the thickness of the intervening uninflated balloon 214. Typically, the tube component 216 will have a consistent frequency of ribs, but may also vary by having intermittent groups of ribs along the tubing.

The balloon and the crimped stent slightly conform to the undulations of the tube component for greater securement, but this conformation is not illustrated.

Tube component 216 may be formed from a thermoplastic material, preferably a low modulus polymer, such as Surlyn™, Pebax and urethane. The device such as polypropylene, low density polyethylene (LDPE), high density polyethylene (HDPE), ethylene vinyl acetate (EVA), nylon, polyester and polyethylene terephthalate ("PET"), may be prepared through free blowing in a mold or inside a coil. Tubing is extruded with relatively thin walls and then free-blown in a mold, coil or other fixture to form the ribs/corrugation.

A balloon 214 for use according to the present invention may be any conventional balloon for catheter delivery, such as a balloon of the type generally used for PTA and PTCA procedures. Typically, balloon 214 is fixed at its distal end to inner shaft 212 near the catheter distal end and at its proximal end to inner shaft 212, near the distal end of the outer shaft 213. Balloon 214 is inflatable through an inflation conduit 223, i.e., the space between coaxial inner shaft 213 and outer shaft 213 of the catheter. The distal and proximal ends of balloon 214 are shown in FIGS. 28 and 29 positioned exterior to the distal and proximal ends of tube component 216, respectively, and of a length L-B generally equal to the length L-T of the tube component 216. To be compatible with the tube component 216 illustrated in FIGS. 28 and 29 and described above, balloon 214 is inflatable at deployment to about the diameter of the body vessel in which the stent 218 is to be deployed. Balloon 214 may be formed of a compliant or non-compliant material, such as polyethylene or any standard balloon material. Compliant materials include low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, polyvinyl chloride, acrylonitrile-butadiene-styrene copolymers, polyether-polyester copolymers, and polyetherpolyamide copolymers. Suitable materials include a copolymer polyolefin material available from E. I. DuPont de Nemours and Co. (Wilmington, Del.), under the trade name Surlyn™ Ionomer and a polyether block amide available under the trade name PEBAX™. Non-compliant materials include relatively rigid stiff high pressure polymeric materials, such as thermoplastic polymers and thermoset polymeric materials, poly(ethylene terephthalate) (commonly referred to as PET), polyimide, thermoplastic polyimide, polyamides, polyesters, polycarbonates, polyphenylene sulfides, polypropylene and rigid polyurethanes, or combinations thereof. The balloon 214 typically has a wall thickness of about 0.0007–0.004 inch for example.

A stent for use according to the present invention may be any conventional type of balloon expandable stent, including stents of the type used for PTA and PTCA angioplasty procedures, for prostate therapy, and TTS endoscopic catheters for gastrointestinal use. Suitable stent material is biocompatible stainless steel in the form of sheet metal, tube component wire or Nitinol. A preferred stent is described in PCT Application No. 960 3072 A1, published Feb. 8, 1996, the content of which is incorporated herein by reference. All such stents are well known in this art generally and additional examples are described in U.S. Pat. No. 5,507,768 to Lau et al.; in U.S. Pat. No. 5,458,615 to Klemm et al.; in U.S. Pat. No. 5,226,899 to Sheiban; in U.S. Pat. No. 4,875,480 to Imbert; in U.S. Pat. No. 4,848,343 to Wallsten et al.; and in U.S. Pat. No. 4,733,665 to Palmaz. Stent 218 as shown in FIGS. 28 and 29 is positioned on balloon 214, which is over the underlying tube component 216, at the distal end of the catheter. The length L-S of stent 218 is shown as essentially equal or slightly smaller than the length L-T of tube component 216 and is positioned on assembly 210 to be coextensive with tube component 216. In this position, stent 218 is shown in FIG. 28 crimped to its delivery diameter D1, which is about 0.035–0.45 inch for example.

As discussed above, despite the most careful and firm crimping of stent 218 to closely conform to the overall profile of the catheter unexpanded balloon 214 and underlying tube component 216, there is a certain amount of "recoil" of stent 218 or a tendency of stent 218 to slightly open from a desired hypothetical minimum crimped diameter. The actual minimum diameter achievable for fully crimped stent 218 on assembly 210 is referred to as stent 218 delivery diameter D1. This tendency of stent 218 to open or recoil slightly when crimped on assembly 210 has been characterized as "recoil crimping". In FIG. 28, tube component 216 is shown inflated to a diameter which is generally sufficient to compensate for any slack or looseness between crimped stent 218 and the overall profile of the catheter, the unexpanded balloon 214 and the underlying tube component 216 due to recoil crimping.

FIG. 29 illustrates a side profile section showing a stent delivery and deployment assembly 210 of this invention with balloon 214 fluid inflated to its fully expanded position. As a result of the fluid inflation of the balloon 214, stent 218 has also been fully expanded to its deployment diameter D2 in which it can be deployed against the walls of a body vessel in which it is situated.

Figure 30:
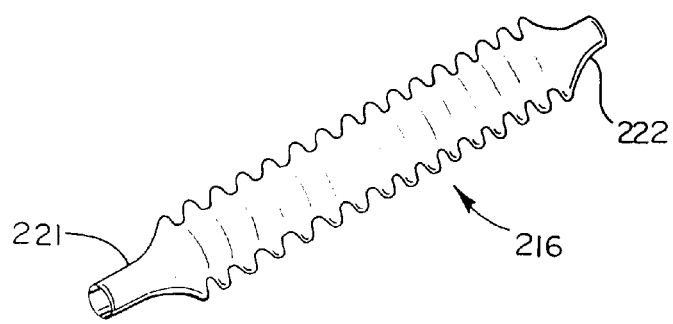
FIG. 30 is a perspective view of the corrugated tubing of the present invention.

FIG. 30 illustrates the preferred configuration of the tube component 216. The tube component has a plurality of ribs 230 and is configured in a corrugated or accordion fashion. The ends of the tube component 216, 222 and 221, are substantially rib-free so as to provide a flat surface to receive an adhesive and thereby bond to the inner shaft 212. Preferable adhesives include cyanocrylates such as Loctite 4061/4011 or urethanes, such as H. B. Fuller 3507/3506. The tube component may also be heat bonded to the inner shaft. The ribs may vary in frequency and spacing.

Figure 31:
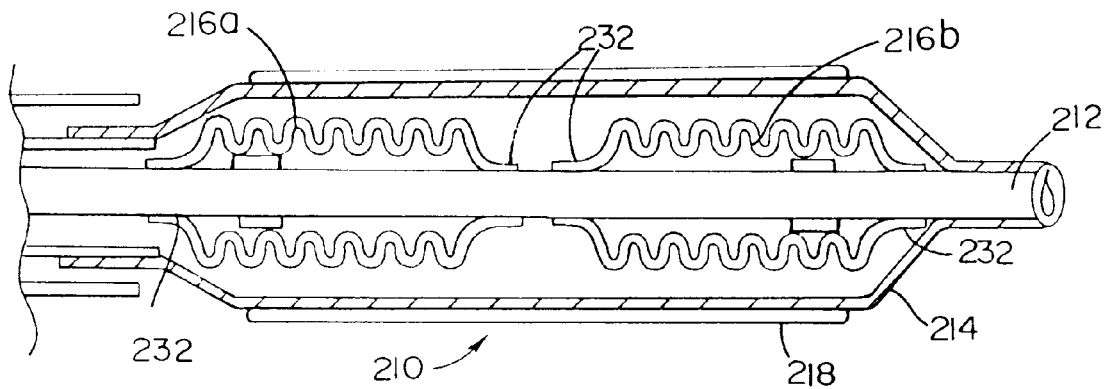
FIGS. 31–33 are side profile sections showing alternative embodiments of balloon expandable stent delivery and deployment assemblies, having the tubing component formed in a plurality of sections.
Figure 32:
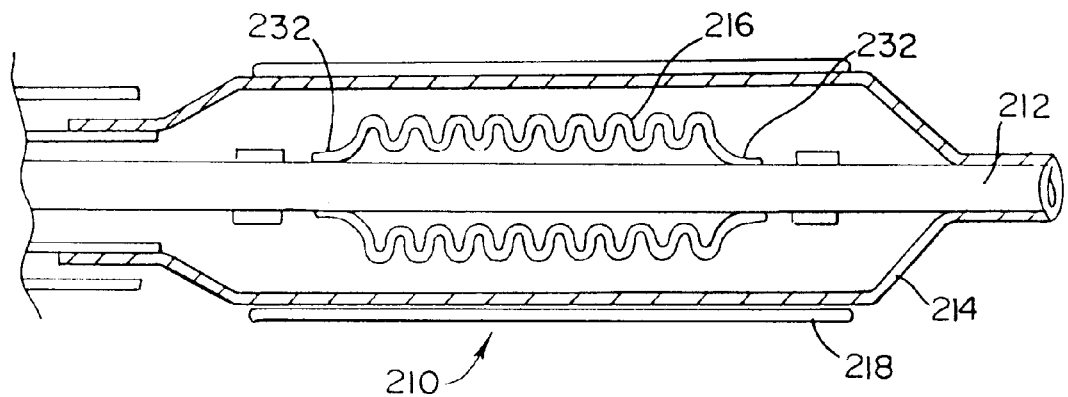
Figure 33:
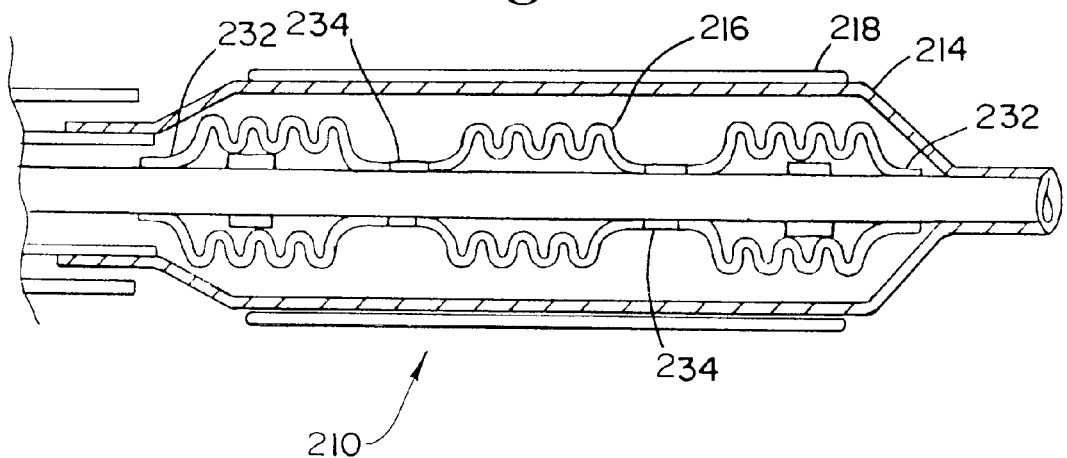

Tube component 216 may have different configurations in other embodiments, as shown in FIGS. 31–33. The tube component 216 may be comprised of more that one piece of corrugated tubing (FIG. 31), a smaller single piece (FIG. 32) or one single piece of tubing sectioned into a plurality of ribbed sections, wherein the tubing is adhered to the inner shaft 212 in more than two locations (FIG. 33).

FIG. 31 shows two pieces of tubing component 216a, 216b. Both pieces are adhered to inner shaft 212 at adhesion points 232. FIG. 32 discloses an embodiment which comprises one smaller piece of tube component 216 which is adhered to inner shaft 212 at adhesion points 232. FIG. 33 discloses an embodiment which comprises one tube component 216 which has interrupted ribbed sections 234 adhered to the inner shaft 212.

Figure 34:
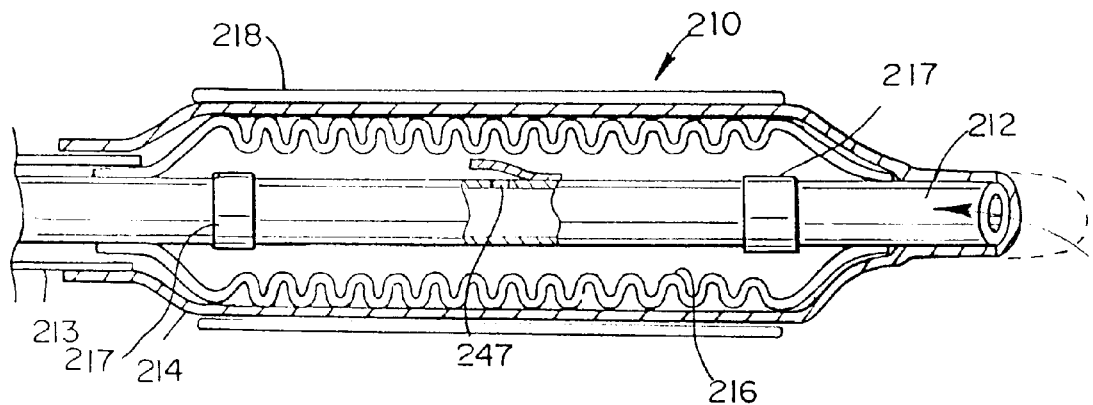
FIGS. 34–35 are side profile sections showing alternative embodiments of the balloon expandable stent delivery and deployment assemblies, the tube component inflatable to add securement pressure.
Figure 35:
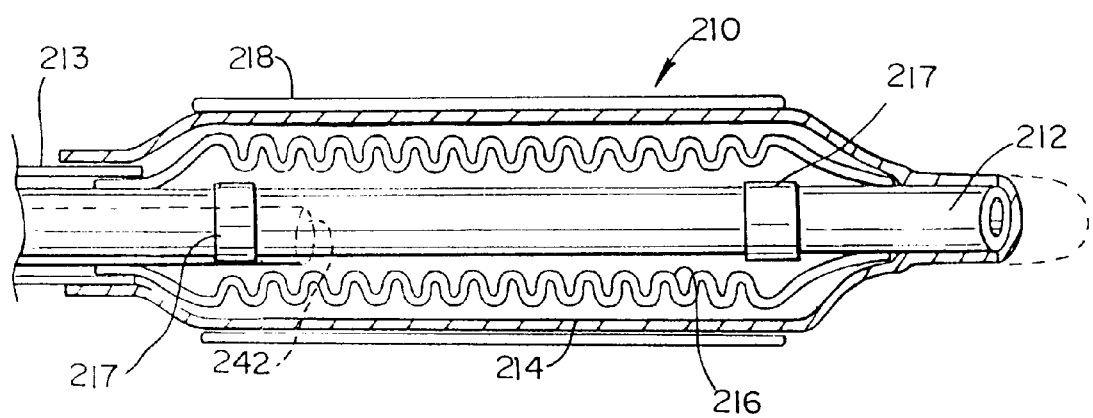

FIGS. 34 and 35 illustrate an alternative embodiment in which the tubing component is inflatable to increase the securement pressure on the inside of balloon 214 when the stent is crimped onto the balloon so as to negated additional recoiling. The full expansion of the tube component 216 should only be slightly greater than the diameter of the inside of the balloon 214 when the stent 218 is fully crimped onto the balloon 214.

In FIG. 34, the inflating fluid comes through the guide wire lumen 212 under pressure from the proximal end or the distal end of the guide wire lumen 212, preferably via a syringe, and fills the tubing component 216 through a one-way valve 247 (preferably resisting up to about 4 atm) in the inner catheter 212.

In FIG. 35, the tubing component 216 is inflated via an additional lumen 242 which extends from the proximal end of the catheter along the guide wire lumen 240, much the same as any inflating lumen incorporated to inflate a balloon.

Figure 36:
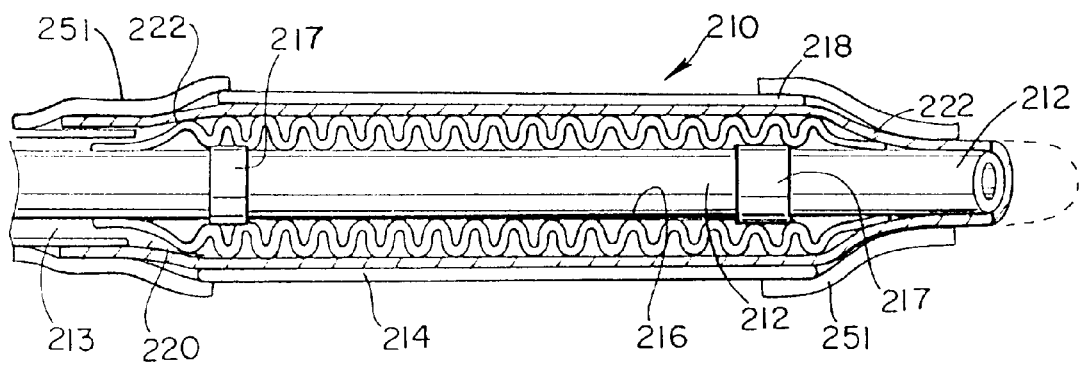
FIG. 36 is a side profile section showing a balloon expandable stent delivery and deployment assembly, with the stent crimped to delivery diameter onto the balloon, the underlying tube component and the catheter, and also having containment sleeves covering the ends of the stent.

In an alternative embodiment, as shown in FIG. 36, socks or sleeves 251 may be incorporated to stretch over the ends of the stent to prevent snagging and to secure the stent onto the balloon. Such sleeves are demonstrated in U.S. application Ser. Nos. 08/702,149, filed Aug. 23, 1996, and 08/701,979, filed Aug. 23, 1996, which are incorporated in their entirety herein by reference.

Figure 37:
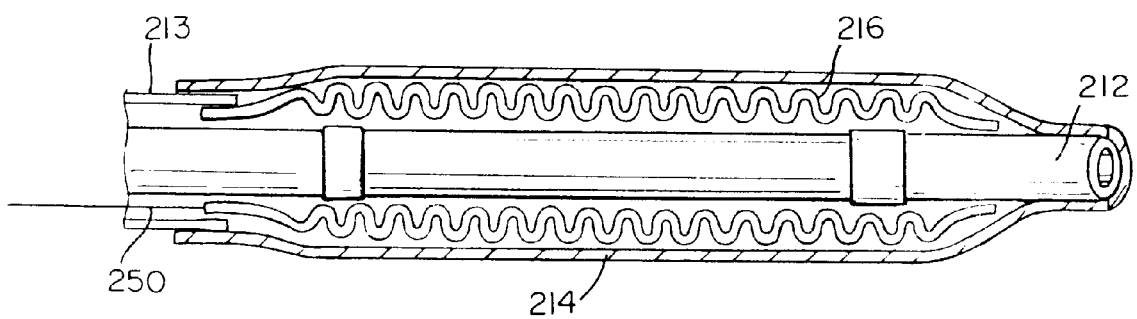
FIG. 37 is a side profile section showing a balloon expandable stent delivery and deployment assembly, with the stent crimped to delivery diameter onto the balloon, the underlying tube component and the catheter, and also having a pull-back wire attached to the tube component.

In still another embodiment, as shown in FIG. 37, the tubing component 216 is slidable axially along the inner shaft 212 and is connected to a retracting wire 250 such that the tubing component may be retracted into the outer shaft 213 after the balloon has been inflated to reduce the profile of the balloon 214 when the catheter is removed. The tubing component, since it is not adhered to the inner shaft 212 in this embodiment, should fit tightly enough on the inner shaft to stay in place, but not too tightly so that it may be retracted by pulling on the retracting wire 250.

The method of using the stent delivery and deployment assembly 210 of this invention, as shown in FIGS. 1 and 2, is described as follows. The assembly 210 is constructed as described above. Stent 218 is compressed or crimped onto balloon 214, tube component 216 and the catheter to a delivery diameter D1. This crimping can be done manually or with the aid of tooling specifically designed for the purpose either by the physician or the manufacturer. In the crimped position, stent 218 closely conforms to the overall profile of balloon 214, tube component 216 and the catheter except for the slight slack or looseness due to recoil crimping. Tube component 216 is flexible enough to slightly collapse during crimping and rebound to the extent necessary to compensate for the slack or looseness due to recoil crimping, thus securing the stent. As a result, the stent does not move out of its position on the catheter during delivery or become separated from the catheter within a body vessel. The catheter distal end is delivered by standard techniques to the deployment site within the body vessel of interest. At this point, stent 218 is positioned as required by the physician and balloon 214 is fluid inflated by standard technique to expand stent 218 to its deployment diameter D2. During this expansion, stent 218 is expanded to fill the body vessel. Following deployment of stent 218, balloon 214 is deflated and the assembly is retracted proximally and withdrawn from the body. If required by the procedure, the site of entry to the body is appropriately closed.

The tube component provided by this invention increases stent securement force by increasing the frictional force between the tube component, the balloon wall and the internal diameter of the stent in its reduced crimped delivery diameter. The tube component is more flexible than a solid sheath under the expandable balloon, and thus the entire assembly has greater flexibility. This invention has particular advantages for assemblies in which the stent is provided for use as pre-crimped to the balloon and underlying catheter, by increasing the shelf life of the pre-crimped assembly. The tube component also protects the balloon material during crimping by acting as a buffer between the balloon material and whatever may be mounted on the inner shaft, such as marker bands 217. The features and principles described for this invention are suitable for use with fixed wire, over-the-wire and single operator exchange assemblies.

Figure 38:
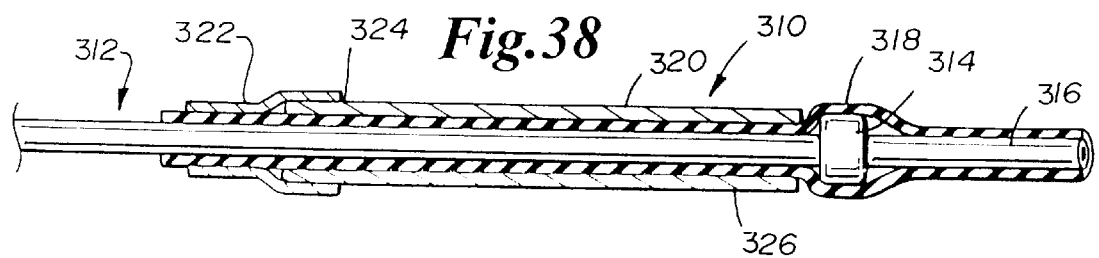
FIG. 38 is a longitudinal cross-section of a stent delivery and deployment assembly of this invention showing a catheter with a collar mounted at the catheter distal end, an uninflated balloon mounted on the catheter over the collar, an unexpanded stent mounted on the balloon abutting the collar and a cup overlying the stent proximal end portion.
Figure 39:
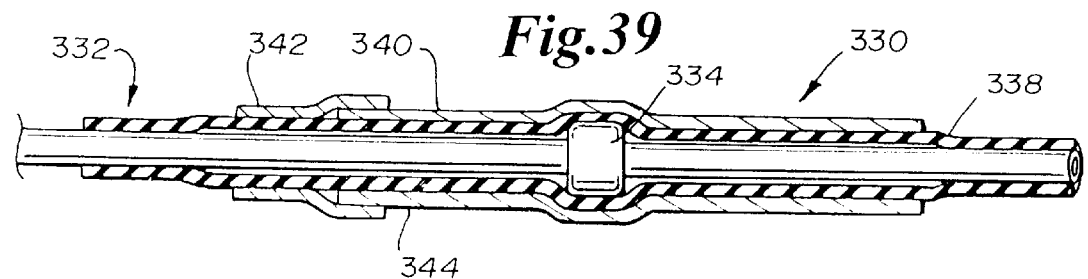
FIG. 39 is a longitudinal cross-section of another stent delivery and deployment assembly of this invention showing a catheter with a collar mounted as a mounting ring at the catheter distal end, an uninflated balloon mounted on the catheter over the mounting ring, an unexpanded stent mounted on the balloon overlying the mounting ring and a cup overlying the stent proximal end portion; note that the collar is positioned closer to the cup than in FIG. 38.
Figure 40:
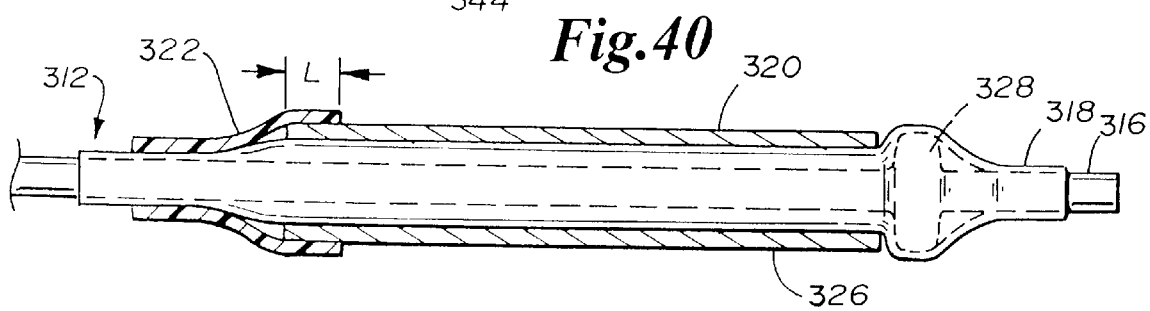
FIG. 40 is a longitudinal profile in partial cross-section of an assembly similar to that of FIG. 38, with a bulge formed under the uninflated balloon at the catheter distal end.

FIGS. 38–46 disclose alternative embodiments of the securement device. FIG. 38 shows a stent delivery and deployment assembly generally designated 310. A catheter 312 has a collar 314 coaxially mounted at the catheter distal end portion 316. An uninflated balloon 318 is coaxially mounted on catheter 312 over collar 314. An unexpanded stent 320 is coaxially mounted on the balloon 318 abutting but not overlying collar 314. A cup 322 coaxially overlies the stent proximal end portion 324. Cup 322 may be elastomeric or rigid, preferably elastomeric. Cup 322 is over-expanded over the stent 320, so that recoil of the cup 322 is sufficient to secure stent 320 in place and prevent it from being pulled off of the assembly 310 distally or proximally as assembly 310 is delivered to a deployment site in a body vessel. Cup 322 also protects the proximal end of stent 324 from inadvertently catching on anatomical structures or other things during maneuvering within the body or during loading and other handling. The ends of the stent may axially protrude and should be protected during maneuvering of stent 320 to keep stent 20 on assembly 310 in its contracted configuration and to maintain the structural integrity of stent 320. Collar 314 abuts the stent distal end 326 without underlying stent 320. The position of cup 322 overlying stent 320 and containing stent 320 against collar 314 increases the securement force maintaining stent 320 in its axial and radial position on catheter 12. FIG. 40 is similar to FIG. 38, showing a bulge 28 beneath the uninflated balloon 318 at catheter distal end 316.

Any of the various types of known stents may be used in the delivery system of this invention, even self-expanding stents which are partly balloon-expandable may be used, the balloon initiating release of the stent and/or finally seating the stent after self-expansion. However, ordinary balloon expandable stents are preferred and aforenoted.

FIG. 39 shows another stent delivery and deployment assembly generally designated 330. A catheter 332 has a collar coaxially mounted as a mounting ring 334 on the catheter. An uninflated balloon 338 is coaxially mounted on catheter 332 over mounting ring 334. An unexpanded stent 340 is coaxially mounted on balloon 338 overlying the mounting ring 34. A cup 342 overlies the stent proximal end portion 344 to secure the stent 340 in place and prevent it from being pulled off of assembly 330 distally or proximally, as assembly 330 is delivered to a deployment site in a body vessel. Cup 342 also protects the proximal end of stent 40 from inadvertently catching on anatomical structures during maneuvering within the body. The position of cup 342 overlying stent 340 together with the closer positioning of mounting ring 334 as compared to FIG. 38 increases the securement force maintaining stent 340 in its axial and radial position on catheter 342. The closer the mounting ring 334 is positioned to cup 342 the more securely the stent is held in place and interlocked between this cup and ring. When used in conjunction with mounting ring 334, cup 342 will also prevent the stent proximal segment 344 from opening up, i.e., increasing its diameter, and will keep the stent 340 locked onto the mounting ring 334. This will prevent stent 340 from moving on the catheter distally as well as proximally. This cup does not have to be an elastomer, but may be sufficiently rigid to prevent the stent 340 from expanding.

Cups 322, 342 of FIGS. 38–40 release stents 320, 340 when balloons 318, 338 are inflated during deployment. Cups 322, 342 can, for example, flare radially outward as illustrated with reference to FIG. 41, roll axially away from stents 320, 340 as illustrated with reference to FIG. 42, or slide axially away from stents 320, 340 as illustrated with reference to FIGS. 43 and 44. Also, the cups may be formed with axial areas of weakness which split on balloon inflation, as described in the aforenoted Savin patent.

Figure 41:
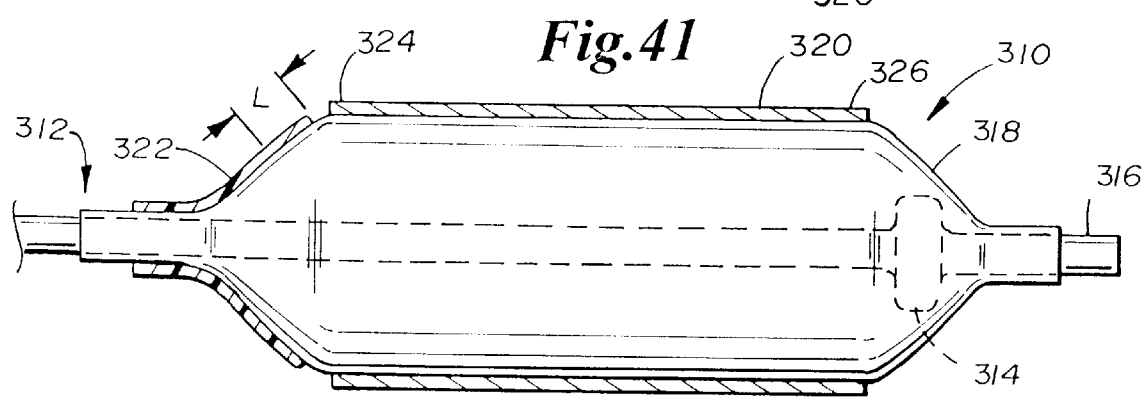
FIG. 41 is a longitudinal profile in partial cross-section of the assembly shown in FIG. 38 with the balloon inflated and the stent expanded, showing the cup end portion flared to release the stent.

FIG. 41 shows an assembly generally designated 310 as shown in FIGS. 38 and 36 with balloon 318 inflated and stent 320 expanded, showing the cup 322 end portion flared to release stent 320. As noted above, cup 322 may be elastomeric or rigid. The dimension L is short enough and the material of cup 322 is sufficiently elastic so that cup 322 flares out and is no longer in contact with stent 320 when balloon 318 is inflated and the stent 320 expanded for deployment.

Figure 42:
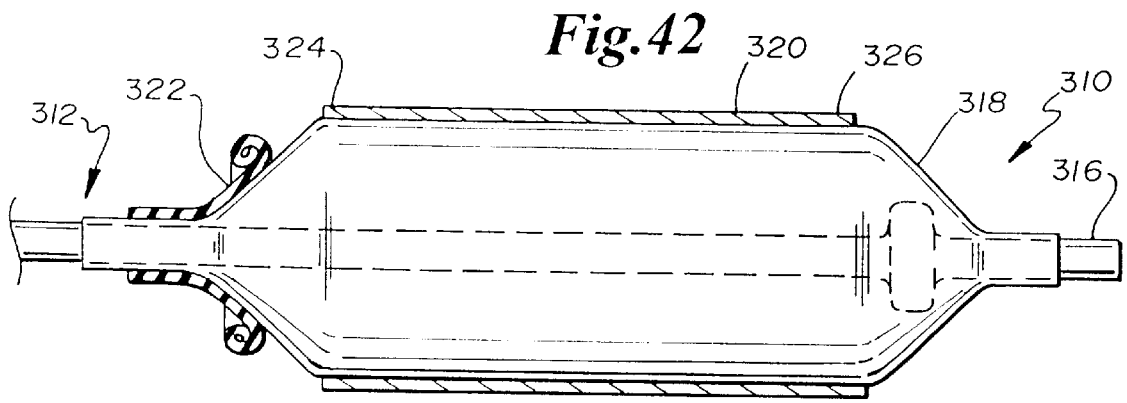
FIG. 42 is a longitudinal profile, similar to FIG. 41, showing the cup end portion rolled proximally to release the stent.

FIG. 42 shows an assembly generally designated 310, as shown in FIGS. 38 and 36, with balloon 318 inflated and stent 320 expanded, showing cup 322 end portion rolled proximally to release the stent 320. As noted above, the cup 322 may be elastomeric to facilitate rolling. The cup may also accordion or bunch up on itself to release the stent.

Figure 43:
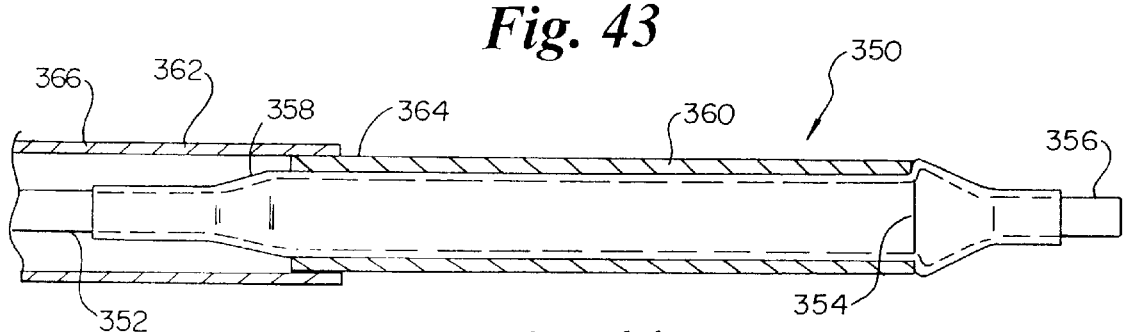
FIG. 43 is a longitudinal profile of yet another stent delivery and deployment assembly of this invention, with the balloon mounted on the catheter, which has a collar formed as a tapered single enlarged piece on the catheter, an unexpanded stent mounted on the unexpanded balloon abutting the collar and a cylindrical sleeve overlying the stent proximal end portion.
Figure 44:
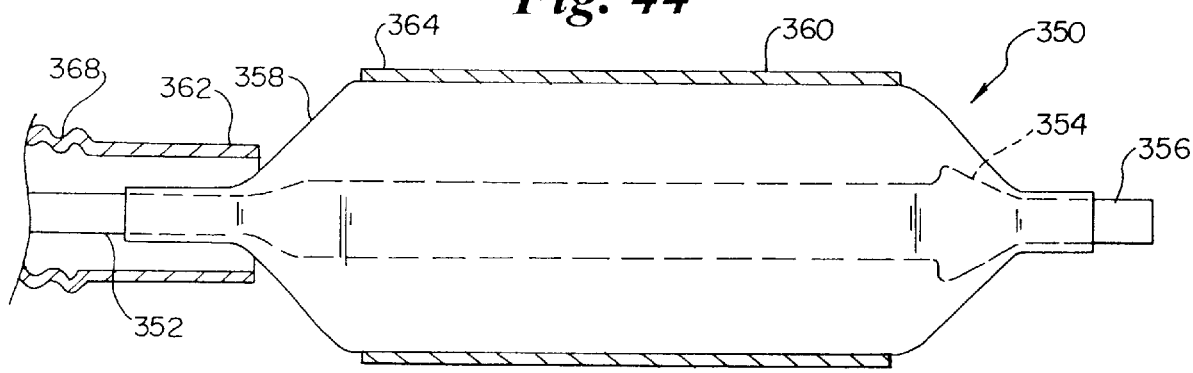
FIG. 44 is a longitudinal profile of the assembly of FIG. 43 with the balloon inflated and the stent expanded, showing the sleeve moved proximally to release the stent

FIGS. 43 and 44 show yet another stent delivery and deployment assembly generally designated 350. The catheter 352 has a coaxial collar 354 formed integrally with catheter 352 at the catheter distal end 356. A balloon 358 is coaxially mounted on catheter 352, overlying collar 354. In FIG. 43, balloon 358 is coaxially mounted on catheter 352, overlying collar 354. In FIG. 43, balloon 358 is shown as uninflated, with an unexpanded stent 360 mounted on balloon 358 abutting collar 354, and a cylindrical cup in the form of sleeve 362 overlying the stent proximal end portion 364. FIG. 44 shows the assembly 350 of FIG. 43 with balloon 358 inflated and stent 360 released and expanded. Sleeve 362 is designed, constructed and adapted so that, as balloon 358 and stent 360 are enlarged, the sleeve portion 366 gathers or moves proximally to release stent 360. The increasing angle of the balloon 358 cone (the tapered end sections of balloon 358) during inflation push sleeve 362 axially away from stent 360. This can be done by shaping sleeve 362 with preformed accordion pleats 368. Sleeve 362 may also be formed so that the portion detaining (that is, abutting or overlying) stent 360 is of thicker or more rigid material than the portion of sleeve 362 axially distant from stent 360. Materials which may be used to provide the foregoing function are silicones, urethanes and the like as well as other elastomers, for example. A rigid sleeve carried on the catheter for sliding movement may also be used. Sleeves may be included at the proximal and distal end of the stent.

Figure 45:
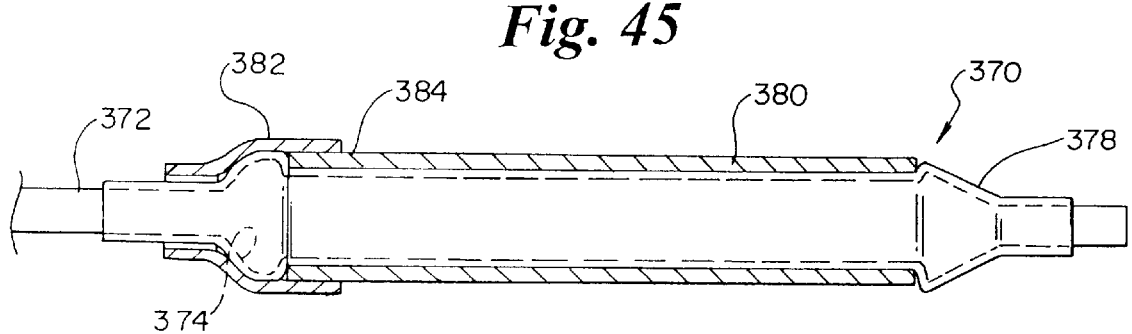
FIG. 45 is a side profile of still another stent delivery and deployment assembly of this invention with the uninflated balloon mounted on the catheter which has two collars formed integrally with the catheter, an unexpanded stent mounted on the balloon abutting the collar and a cylindrical cup overlying the stent proximal end portion and the underlying collar.

FIG. 45 shows still another stent delivery and deployment assembly generally designated 370. A catheter 372 has two collars 374 formed integrally with catheter 372 and spaced from each other on the catheter distal end portion. A balloon 378 is coaxially mounted on the catheter 372, overlying the collars 374. The balloon 378 is shown as uninflated with an unexpanded stent 380 mounted on balloon 378 abutting both of the collars 374. It can be seen that the distance between the collars 374 is to be chosen to closely accommodate stent 380 in its fully contracted position about the balloon 378 and underlying catheter 372. A cup 382 overlies the stent proximal end portion 384 and the underlying proximal collar 374. Cup 382 will deploy during balloon 378 inflation in the manner described above with reference to FIGS. 41–44.

Figure 46:
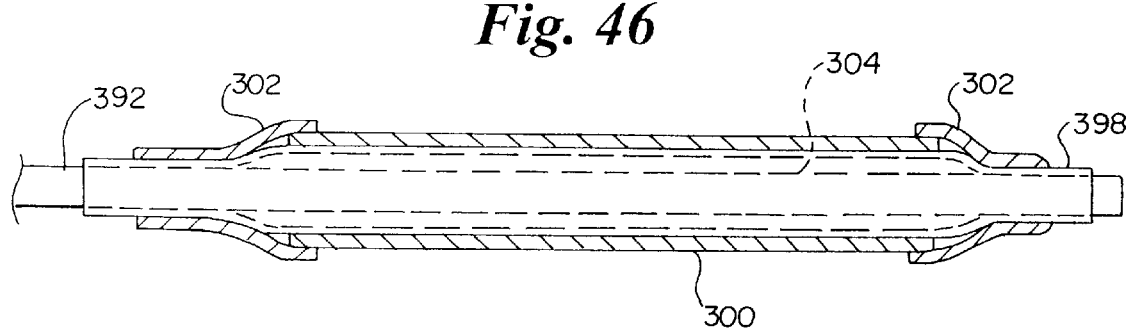
FIG. 46 is a longitudinal profile of another stent delivery and deployment assembly of this invention with the uninflated balloon mounted on the catheter, an unexpanded stent mounted on the balloon, mounting a cylinder on the catheter and a pair of cups overlying the stent ends.

FIG. 46 shows even another stent delivery and deployment assembly generally designated 390. The uninflated balloon 398 is shown coaxially mounted on a catheter 392 at the catheter distal end portion. An unexpanded stent 400 is coaxially mounted on balloon 398. A pair of cups 402 overlap the ends of the stent 400 ends. A mounting cylinder 404 is carried by the catheter shaft 392.

The Figure also illustrates cups at both ends of the stent, an arrangement which may be used in all the foregoing embodiments.

The cups or sleeves used in the various embodiments of this invention can be of elastomeric or rigid material to contain one or both ends of the stent. In preferred embodiments of this invention the cups are used in conjunction with one or more stent collars positioned under the balloon. The collar may be formed as a ring, to abut the end of the stent, to lie under the stent and the intervening balloon, or as a cylinder, to lie under essentially the entire length of the stent and the intervening balloon. The stent detainment according to the present invention offers increased stent securement, particularly on pre-mounted delivery systems. The cups and sleeves illustrated in the various embodiments of this invention can be secured to the catheter, as by adhesive or thermal bonding, or they may be sliding cups or sleeves. When the cups are freely sliding on the catheter, they should always be used directly over a collar so that there is a friction fit between the cup and the stent.

A method for delivering and deploying a stent using an assembly according to the present invention is described as follows: A catheter is provided as described above with reference to any of FIGS. 38–40, 43 and 45. At least one collar is coaxially mounted at the catheter distal end. As discussed above, the collar may be a separate element affixed to the catheter or the collar and catheter may be formed together as a single element. The collar may be positioned abutting an end of the stent. The collar may be a mounting ring, may be positioned under the stent or underlying the balloon. The collar may be a cylinder essentially coextensive in length with the stent and underlying the balloon. A fluid expandable balloon is coaxially mounted over the collar on the catheter distal end. A stent is provided which is inflation expandable from a reduced to an enlarged condition. The stent, in its reduced condition, is coaxially mounted on the balloon so that at least an end portion of the stent overlies the balloon. A cup is provided which has first and second end portions. The cup is in an expanded form and also has a retracted form. The expanded cup is coaxially mounted on the catheter at the distal end portion so that the cup first end portion detains the stent end portion. The cup first end portion detains the stent end portion by overlying the stent end portion, or by closely accommodating the stent against the collar without overlying the stent end portion. The cup is then contracted about the catheter and the stent end portion to fix the stent to the catheter. The cup and collar cooperate to retain the stent on the catheter in its reduced condition. The assembly is then maneuvered by the physician through a body vessel by methods known per se to reach a pre-selected deployment site. The surgeon can determine when the assembly has reached the deployment site by means which are themselves known per se. For example, the assembly may be provided with radiopaque marking bands at either end of the stent, or the cups or the collars or both may be made of radiopaque material. Once the surgeon determines that the stent has been correctly positioned at the desired site, the balloon is inflated to expand the stent to its enlarged condition. Inflation of the balloon expands the stent and the stent is released from the cup or cups. As has been discussed above, the cups may deploy to release the stent in a number of ways, dependant on the construction and materials of the cup or cups. The cup may flare or enlarge radially following the increasing angle of the balloon cones. The cup may roll axially away from the stent. The portion of the cup axially distant from the stent may accordion back on itself. The cup may slide axially. The cup may accordion or buckle. If the cup is not fixed to the catheter, but is freely slidable on the catheter, the cup may slide axially away from the stent. After deployment of the stent, the balloon, according to previously known procedures, is deflated and the assembly is withdrawn proximally from the body vessel. Any incision made to allow access from the assembly is appropriately closed.

Figure 47:
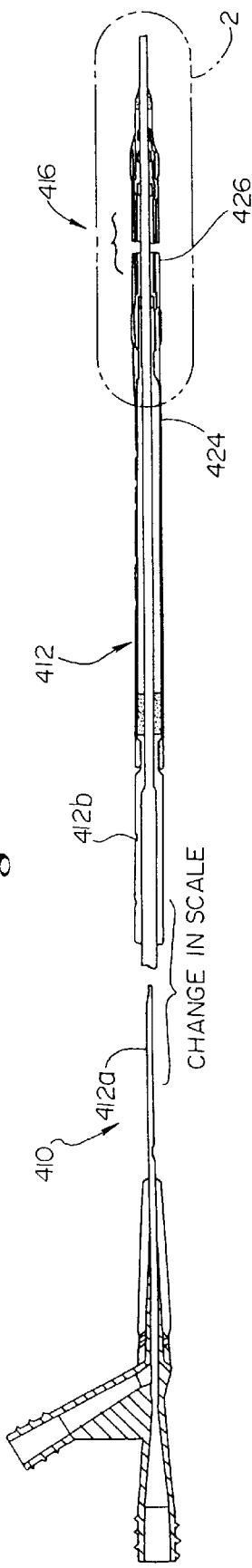
FIG. 47 is an isometric view, a portion of which is enlarged and in longitudinal section, of a balloon catheter having a stent fixed to the catheter over the balloon.
Figure 48:
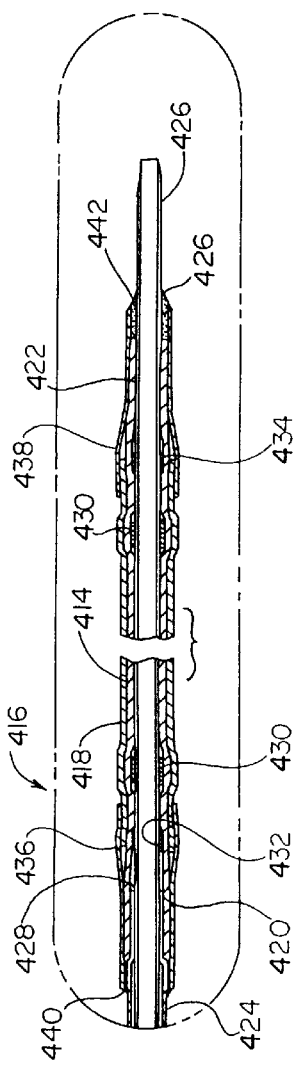
FIG. 48 is an even more enlarged view in longitudinal cross-section of the distal end portion of the catheter of FIG. 47.

FIGS. 47–56 illustrated alternative embodiments of securement devices. Referring to FIGS. 47 and 48 a stent delivery system generally indicated at 410 includes a balloon catheter 412 having a balloon 414 on a distal end portion generally indicated at 416. FIG. 47 shows a proximal portion of the catheter at 412a and a distal portion 412b in enlarged view. FIG. 48 shows the distal end portion 416 in an even more enlarged view. The illustrative catheter 412 is of the type known as an over the wire catheter. However, other types of catheters may be used, such as rapid exchange/single operator exchange and fixed wire types. The balloon 414 is fixed to the catheter 412 by standard means. The balloon is shown in its contracted state in FIGS. 47 and 48. A stent 418 is fixed about the balloon by crimping it thereto. The stent has a larger expanded diameter which is obtained when the balloon is expanded in the known manner. That is, the stent is released from the catheter upon expansion of the balloon when placed in a vessel. When the balloon is then deflated, removal of the balloon and catheter may be accomplished while leaving the stent in place.

As is known in the art the balloon is either bonded at its ends by adhesive 420 and 422, respectively to the outer member 424 of the catheter and to the inner member 426 of the catheter in the manner as shown, or is made one-piece with the outer member as is known in the art. The catheter balloon may be inflated by fluid (gas or liquid) from an inflation port extending from a lumen 428 contained in the catheter shaft and opening into the balloon as shown, or by other known arrangements, depending on the design of the catheter. The details and mechanics of balloon inflation and specific overall catheter construction will vary according to the particular design involved in any given instance, and are known in the art per se. All variations are acceptable for use with this invention.

Any balloon expandable stent may be used with this invention. Many are known in the art including plastic and metal stents. Some are more well known such as the stainless steel stent shown in U.S. Pat. No. 4,735,665; the wire stent shown in U.S. Pat. No. 4,950,227; another metal stent shown in European Patent Application No. EP0 707 837 A1 and that shown in U.S. Pat. No. 5,445,646. All of these patents are incorporated herein by reference. Also, shape memory metal stents may be used. As already indicated the stent of PCT Application 960 3092 A1 is particularly preferred.

The stent is typically about 16 mm long, while the balloon may be 20 mm long. These dimensions, however, are merely representative for illustrative purposes only and are not meant to be limiting. The stent is positioned over the balloon portion of the dilatation catheter and gently crimped onto the balloon either by hand or with a tool such as a pliers or the like to be mounted for delivery as shown in FIGS. 47 and 48. The crimping may be accomplished by either the manufacturer or the physician.

In accordance with one embodiment of this invention, a mounting bodies 430, seen in FIGS. 47 and 48 are included inside balloon 414 to provide a cushion and/or substrate of enlarged diameter relative to the shaft to support and hold the stent and secure it during crimping and the delivery procedure. The mounting bodies are preferably located in the body portion of the balloon.

In the embodiment shown, mounting bodies 430 are ring-like in form and are mounted on inner lumen 426, providing an enlarged area or portion for receiving the balloon and stent when the latter is crimped. Marker bands 432 and 434 may also be included on inner 426 as shown. Any radiopaque material such as gold is useful for this purpose. Although, the material of the mounting bodies may be hard, it is preferably of any thermoplastic elastomer having elastic or deformable properties, more preferably of a relatively resilient elastomer material, e.g., silicone, preferably a lower durometer silicone, or polyurethane, such as Tecothane 1055D. A deformable thermoplastic material such as high density polyethylene (HDPE) may be used. Any deformation of resilient material of the mounting body when the stent/balloon is crimped to it causes a radial outward force on the stent/balloon increasing the friction therebetween despite a recoil of the stent.

The stent is also fixed in position by two overlying retaining sleeves 436 and 438. Sleeves 436 and 438 are formed of polyurethane, preferably Tecothane 1055D, and are axially fixed on catheter 412 by adhesive plugs 440 and 442 of urethane adhesive. The plugs of adhesive may be tapered to the catheter as shown to facilitate movement of the catheter in a vessel. The sleeves overlap the marginal end portions of stent 418 as shown.

A lubricating solution such as silicone fluid may be used between balloon 414 and sleeves 436 and 438 and thereon to facilitate release of stent 418 from the sleeves.

Figure 49:
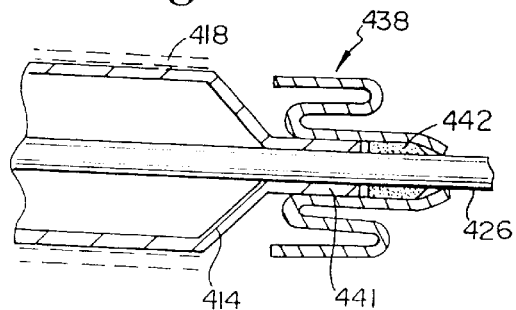
FIG. 49 is a schematic showing of one form of retraction of the releasable sleeve upon expansion of the balloon.
Figure 50:
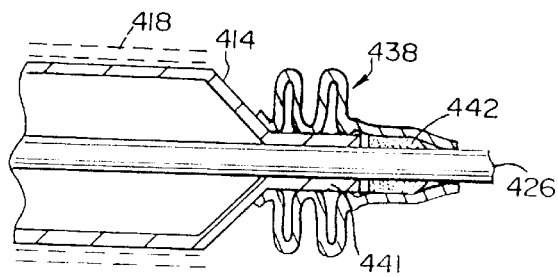
FIG. 50 is a schematic showing of another form of retraction of the releasable sleeve upon expansion of the balloon.
Figure 51:
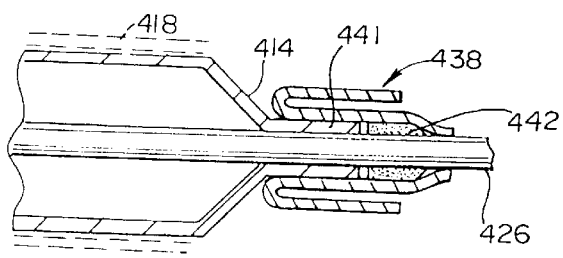
FIG. 51 is yet another form of retraction of the releasable sleeve upon expansion of the balloon.
Figure 52:
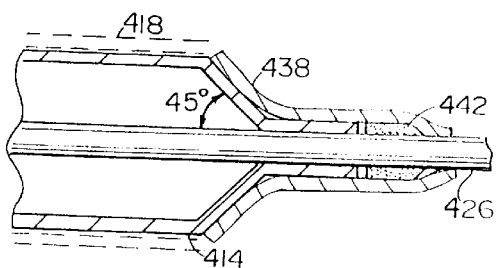
FIG. 52 is a schematic showing of yet another form of retraction of the releasable sleeve upon expansion of the balloon.

During delivery, the balloon catheter is advanced through and positioned in a patient's vasculature so that the stent is adjacent to the portion of the vessel where treatment is to take place. The balloon is inflated to expand the stent to an enlarged diameter. At this time, expansion of the balloon causes the end margin of the sleeves to slide axially from over the stent thereby releasing the ends of the stent from the catheter. Various forms of retraction of sleeves 436 and 438 are shown in FIGS. 49–52. These figures illustrate the configuration of the sleeves 436 and 438 in their retracted state after the balloon 414 has been fully expanded. Only the distal sleeve 438 is shown. FIG. 49 illustrates the preferably retraction configuration. To promote easier retraction sleeves are coated with silicone. The sleeves are preferably adhered to the outer shaft 424 and the inner shaft 426 at point 440, 442, but may be adhered further up the waste 441 of the balloon. The retraction configurations may be controlled by either pre-creasing the sleeves or adhering the sleeve to a point further up on the waist of the balloon. The sleeves have a tendency of folding at a pre-fold crease or at the point of adherence. A preferred cone angle of 45° for the balloon is shown in FIG. 52, which shows an expanded balloon 414 and retracted sleeves 436,438. When the stent has reached the desired diameter, the balloon is deflated so that the catheter may be removed leaving the stent in place.

Figure 53:
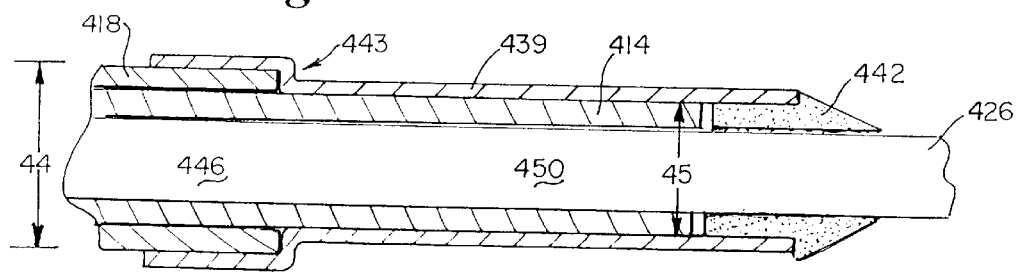
FIG. 53 is a schematic showing of a modified shape for the releasable sleeve.

A modified 439 sleeve configuration is shown in FIG. 53 in stepped form 43 having a large diameter at 444 in one section 446 and a small diameter 445 in a second section 450.

Figure 54:
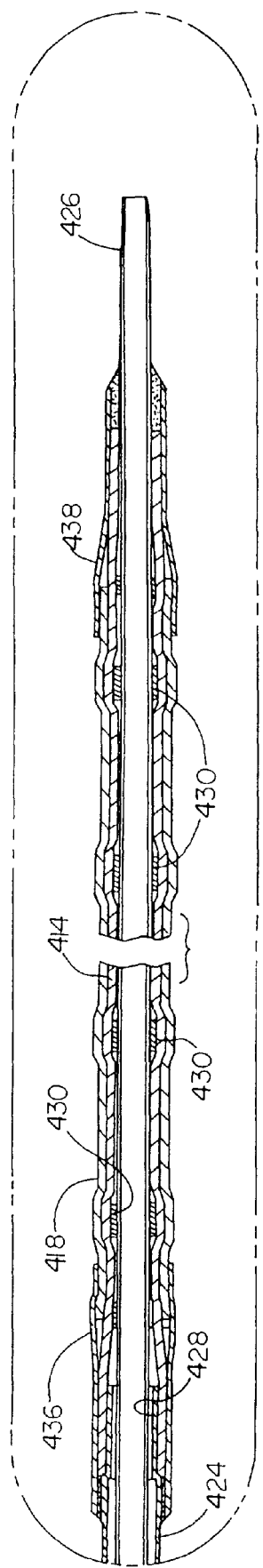
FIG. 54 is a schematic showing in cross-section of another embodiment of the invention with a stent not yet mounted.
Figure 55:
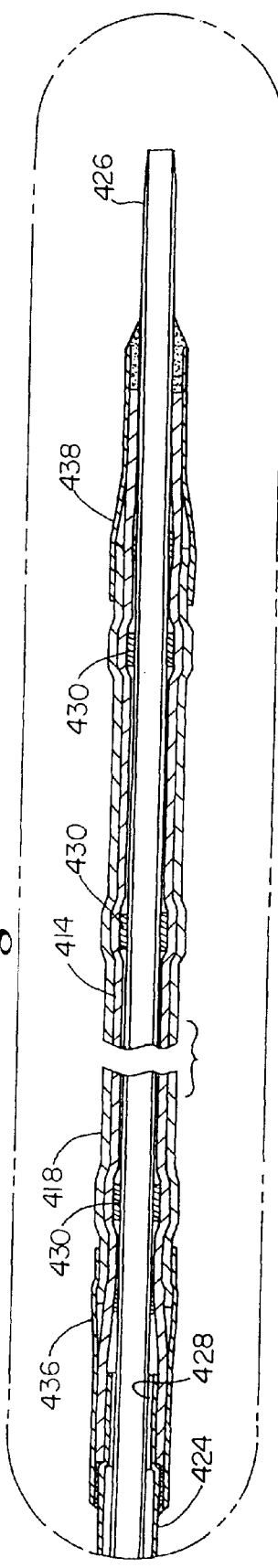
FIG. 55 is a schematic showing of another embodiment of the invention.
Figure 56:
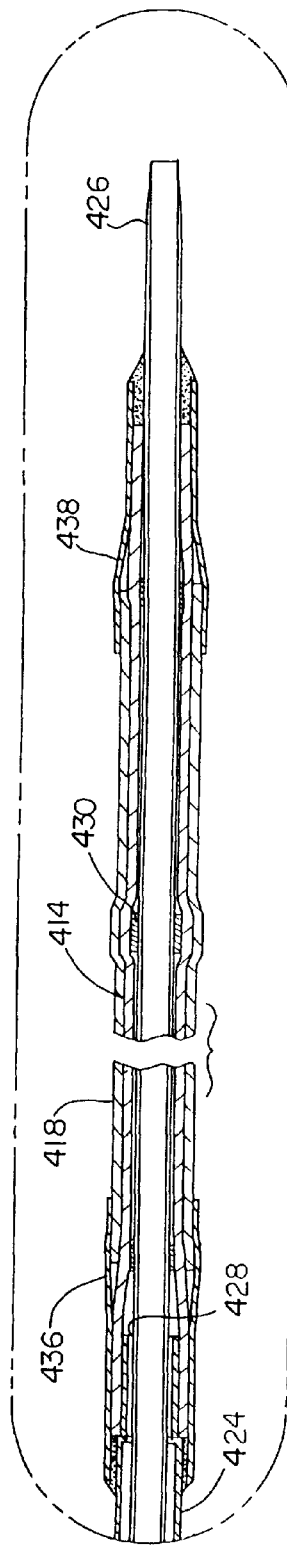
FIG. 56 is a schematic showing of yet another embodiment of the invention.

FIGS. 54–56 show alternative embodiments of the invention. Specifically, alternative positioning and number of mounting bodies 430. These figures show an unexpanded balloon having the mounted bodies 430 within the balloon. They are meant to illustrate essentially the same structure as shown in FIG. 448 differing only in the number and positioning of the mounted bodies 430. In the embodiment shown in FIG. 54, the ring-like mounting body 430 is singular. Another similar version is shown in FIG. 55 which includes three ring-like mounting bodies 430. The embodiment shown in FIG. 56 includes four ring-like mounting bodies 430.

It should be understood that the various elements and materials of all embodiments could be utilized in each of the other embodiments, if desired.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A system/assembly for delivery and deployment of an inflation expandable stent within a vessel, comprising:
   a catheter having proximal and distal ends;
   a stent, inflation expandable from a delivery diameter to a deployment diameter, such that the delivery diameter is reduced from the deployment diameter for conforming the stent to the catheter, such that the stent, in its delivery diameter, is coaxially mounted on the catheter near the catheter distal end;
   an expandable inflation means coaxially mounted on the catheter within the stent, for expansion of the stent from the delivery diameter to the deployment diameter upon application of deployment pressure to the expandable inflation means; and
   a mounting and retaining means coaxially mounted on the catheter within the expandable inflation means, the mounting and retaining means designed and adapted to provide a securement for the stent in the delivery diameter to maintain the stent in position on the catheter during delivery to the deployment site,
   the catheter having a shaft and the expandable inflation means being positioned at a distal part of the shaft, the mounting and retaining means being positioned for receiving the stent on the expandable inflation means for radial expansion of the stent upon expansion of the expandable inflation means, the mounting and retaining means including at least one mounting body carried by the shaft inside the expandable inflation means whereby the diameter of the shaft and expandable inflation means are increased at the distal part for facilitating the mounting and retaining of the sent, the mounting body including at least one separation, whereby the flexibility of the body and catheter is increased.

2. The system of claim 1 wherein the mounting body is substantially the same length as the stent.

3. The system of claim 1, the inflatable means being a balloon, wherein the mounting body is carried by the catheter and is axially movable between the stent mounting position associated with the balloon and a position removed from the stent mounting position.

4. The system of claim 1, further comprising a first sleeve at the distal end of the catheter having a first end gripped to the catheter and a second end overlying a first end portion of the stent, the sleeve releasing the stent upon expansion of the expandable inflation means.

5. The delivery system of claim 4 wherein the mounting body is axially movable with respect to the inside shaft, and including means for moving the mounting body.

6. The stent delivery system of claim 5 wherein the mounting body is of a material which resiliently deforms under radial pressure.

7. The stent delivery system of claim 6 wherein the material comprises HDPE or silicone.

8. The stent delivery system of claim 5 wherein the mounting body includes a plurality of separations along the length of the mounting body.

9. The stent delivery system of claim 1 wherein the separation is in the form of a spiral.

10. The stent delivery system of claim 3 wherein the mounting body is positionable to receive a stent and a stent is crimped to the mounting and retaining means over the balloon for delivery.

11. The stent delivery system of claim 8 including a stop positioned at the distal end portion of the inflatable means and carried by the shaft inside the inflatable means.

12. The stent delivery system of claim 4 further comprising a second sleeve at the distal end of the catheter, having a first end gripped to the catheter and a second end overlying a second end portion of the stent, the sleeves releasing the stent upon expansion of the expandable inflation means.

13. The stent delivery system of claim 8 wherein the the plurality of separations are substantially parralel and substantially circumferentially positioned around the mounting body.

14. The stent delivery system of claim 9 including a stop positioned at the distal end of the catheter and carried by the shaft inside the inflatable means.

15. The stent delivery system of claim 9 wherein the mounting body is a slidably carried coil.

16. The stent delivery system of claim 14 wherein the enlarged mounting body is of a material which resiliently deforms under radial pressure.

17. The stent delivery system of claim 16 wherein the material is elastomeric.

18. The stent delivery system of claim 16 wherein the material comprises polyurethane.

19. The stent delivery system of claim 11 including marker bands positioned on the shaft proximally and distally of the stent.

20. The stent delivery system of claim 9 wherein the separation is substantially along the entire length of the mounting body.

21. The stent delivery system of claim 9 wherein the mounting body is substantially the same length as the stent.

22. The stent delivery system of claim 14 including marker bands positioned on the shaft proximally and distally of the stent.

* * * * *